US011179299B2

(12) United States Patent
Young et al.

(10) Patent No.: US 11,179,299 B2
(45) Date of Patent: Nov. 23, 2021

(54) SYSTEM AND METHOD FOR APPLYING ORAL CARE AGENTS

(71) Applicant: KONINKLIJKE PHILIPS N.V., Eindhoven (NL)

(72) Inventors: Nigel David Young, Surrey (GB); James Donald Gwyer, Great Chesterfield (GB); Hermann Christian Reccius, Cambridge (GB); Zeynep Sabah, Cambridge (GB); Veena Mohan, Cambridge (GB); Estelle Julie Dorothee Bernard-Fichet, Cambridge (GB); Antonius Wilhelmus Maria De Laat, Den Dungen (NL); Johan Lub, Valkenswaard (NL); Nicolaas Petrus Willard, Valkenswaard (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 41 days.

(21) Appl. No.: 15/035,619

(22) PCT Filed: Nov. 14, 2014

(86) PCT No.: PCT/EP2014/074549
§ 371 (c)(1),
(2) Date: May 10, 2016

(87) PCT Pub. No.: WO2015/071386
PCT Pub. Date: May 21, 2015

(65) Prior Publication Data
US 2016/0296427 A1    Oct. 13, 2016

(30) Foreign Application Priority Data
Nov. 14, 2013  (EP) .................................... 13192958

(51) Int. Cl.
| A61K 8/04 | (2006.01) |
| A61K 8/31 | (2006.01) |
| A61K 8/34 | (2006.01) |
| A61Q 11/00 | (2006.01) |
| A61K 8/42 | (2006.01) |
| A61K 8/37 | (2006.01) |
| A61K 8/02 | (2006.01) |
| A61K 8/22 | (2006.01) |
| A61K 8/64 | (2006.01) |
| A61K 8/65 | (2006.01) |
| A61K 8/81 | (2006.01) |

(52) U.S. Cl.
CPC ............ *A61K 8/044* (2013.01); *A61K 8/0233* (2013.01); *A61K 8/22* (2013.01); *A61K 8/31* (2013.01); *A61K 8/34* (2013.01); *A61K 8/37* (2013.01); *A61K 8/42* (2013.01); *A61K 8/64* (2013.01); *A61K 8/65* (2013.01); *A61K 8/8152* (2013.01); *A61Q 11/00* (2013.01); *A61K 2800/884* (2013.01)

(58) Field of Classification Search
CPC .......... A61K 8/8152; A61K 8/31; A61K 8/37; A61K 8/22; A61K 8/0233; A61K 8/044; A61K 8/34; A61K 8/65; A61K 8/64; A61K 8/42; A61K 2800/884; A61Q 11/00
See application file for complete search history.

(56) References Cited

U.S. PATENT DOCUMENTS

| 5,276,068 A | 1/1994 | Waknine |
| 5,444,104 A | 8/1995 | Waknine |
| 5,766,435 A | 6/1998 | Liao et al. |
| 6,013,694 A | 1/2000 | Jia et al. |
| 6,319,510 B1 * | 11/2001 | Yates ..................... A61K 9/006 424/402 |
| 6,740,267 B1 * | 5/2004 | Sekino ................. A61C 13/083 264/19 |
| 2002/0006422 A1 | 1/2002 | Koda et al. |
| 2002/0197214 A1 | 12/2002 | Bublewitz et al. |
| 2004/0028624 A1 | 2/2004 | Bublewitz et al. |
| 2004/0057910 A1 | 3/2004 | Lee et al. |
| 2004/0241110 A1 | 12/2004 | Lee |
| 2004/0241620 A1 | 12/2004 | Allred et al. |
| 2005/0100514 A1 | 5/2005 | Sakaguchi et al. |
| 2005/0113510 A1 | 5/2005 | Feldstein et al. |
| 2005/0220724 A1 | 10/2005 | Busch et al. |
| 2005/0249677 A1 | 11/2005 | Malcmacher et al. |
| 2005/0260544 A1 * | 11/2005 | Jones ................... A61K 8/0208 433/217.1 |
| 2005/0281757 A1 * | 12/2005 | Ibrahim ............... A61K 8/0208 424/49 |

(Continued)

FOREIGN PATENT DOCUMENTS

| CN | 1764433 A | 4/2006 |
| GB | 2190917 A | 12/1987 |

(Continued)

OTHER PUBLICATIONS

Brunton et al: "Treatment of Early Caries Lesions Using Biomimetic Self-Assembling Peptides—A Clinical Safety Trial"; British Dental Journal 215, E6 (2013), 12 Page Document.

(Continued)

*Primary Examiner* — Lezah Roberts

(57) ABSTRACT

A system for providing an oral care agent includes a first layer containing the oral care agent and a second layer. The first layer can be applied directly to teeth. The second layer can subsequently be applied onto the first layer to inhibit leakage of the oral care agent outwards into the mouth.

1 Claim, 16 Drawing Sheets

(56) References Cited

U.S. PATENT DOCUMENTS

| | | | |
|---|---|---|---|
| 2005/0281858 A1* | 12/2005 | Kloke | A61L 27/34 424/423 |
| 2006/0029908 A1 | 2/2006 | Allred et al. | |
| 2006/0064227 A1 | 3/2006 | Uhde et al. | |
| 2006/0171905 A1 | 8/2006 | Allred | |
| 2006/0171906 A1* | 8/2006 | Singh | A61K 8/0208 424/53 |
| 2011/0009834 A1 | 1/2011 | Asmussen et al. | |
| 2012/0093741 A1 | 4/2012 | Maletz et al. | |
| 2013/0078195 A1 | 3/2013 | Chen | |

FOREIGN PATENT DOCUMENTS

| | | |
|---|---|---|
| JP | 2004315460 A | 11/2004 |
| JP | 2006508928 A | 3/2006 |
| JP | 2013522193 A | 6/2013 |
| RU | 2283081 C1 | 9/2006 |
| WO | 03000216 A1 | 1/2003 |
| WO | 2004028497 A1 | 4/2004 |
| WO | 2004028499 A1 | 4/2004 |
| WO | 2004071323 A2 | 8/2004 |
| WO | 2009124311 A1 | 10/2009 |
| WO | 2011112193 A1 | 9/2011 |
| WO | 2013084121 A2 | 6/2013 |
| WO | 2013093877 A2 | 6/2013 |
| WO | 2013128328 A2 | 9/2013 |
| WO | 2014097053 A1 | 6/2014 |

OTHER PUBLICATIONS

Wikipedia: "Solvent" Wikipedia article on solvent, originally downloaded Apr. 10, 2018, 17 page document.

* cited by examiner

SYSTEM AND METHOD FOR APPLYING ORAL CARE AGENTS

CROSS-REFERENCE TO PRIOR APPLICATIONS

This application is the U.S. National Phase application under 35 U.S.C. § 371 of International Application No. PCT/EP2014/074549, filed on Nov. 14, 2014, which claims the benefit of European Patent Application No. 13192958.0, filed on Nov. 14, 2013. These applications are hereby incorporated by reference herein.

FIELD OF THE INVENTION

The invention relates to the dental care arts, and related arts and more specifically concerns a method for applying an oral care agent in the form of a varnish composition.

BACKGROUND OF THE INVENTION

Oral care agents can be applied to teeth via varnish compositions that release the agents into the teeth as moisture from the teeth ingresses through the inner surface of the varnish. The use of varnish compositions as a carrier for oral care agents, brings about several advantages. Particularly, applying a liquid varnish composition onto the teeth can be done easily. This is, e.g., by painting or other spreading techniques such as by using a syringe, brush, or spatula.

A particular advantage is that dental trays, or other invasive application devices, can be avoided, as a varnish composition can be painted or otherwise be manually spread onto the teeth. This is of benefit in a professional care environment, but also allows patients or users to apply such oral care composition by themselves.

However, wetting of the outer surface of the varnish can cause the oral care agents to leak into the mouth (e.g., towards the lips) in addition to into the teeth, thereby reducing the amount of oral care agent delivered to the teeth. The varnish composition may also be soft and easily washed away, thereby not allowing an effective amount of the oral care agent to be delivered to the teeth. The deposited varnish composition may also have a rough surface that can irritate the lips and other soft tissues. Furthermore, the deposited composition may have an undesirable appearance in terms of a rough surface, poor color, and/or undesirable reflectance properties.

The foregoing issues are recognized in the art. A reference in this respect is US 2005/0249677 A1. Therein reference is made to a bleaching method that involves painting a bleaching composition directly onto a person's teeth. It is thereby mentioned that a perceived advantage of paint-on bleaching is that it eliminates the need for a dental tray, but that the main disadvantage of a paint-on bleaching composition is that it remains directly exposed to the person's saliva and disruptive forces found in a person's mouth. In the reference, it is foreseen to apply a dental bleaching composition onto the teeth, applying a protective composition on or adjacent to gingival tissue, and placing a moisture-resistant barrier layer over the tooth surface to be bleached. The barrier layer is a shaped device, e.g., in the form of a dental tray, sheet, strip, or patch. Therewith, i.e., by providing a shaped device to be placed in the mouth, the reference largely reduces, if not altogether diminishes, the advantages associated with applying the oral care agent via a composition that can be painted onto the teeth.

It is desired to provide a system and method are which can overcome some of the problems with existing systems, such as having a reduced leakage rate of an oral care agent into a mouth, but which is fully based on varnish-type composition. i.e., a system and method is sought that is entirely based on compositions that can be easily applied onto tooth surfaces as a fluid, and which are thereafter cured.

SUMMARY OF THE INVENTION

In order to better address the foregoing desires, the invention, in one aspect, presents a system for providing an oral care agent to a tooth, the system comprising a first layer including the oral care agent and a second layer configured to be spaced from a surface of the tooth by the first layer, wherein the first layer comprises a first solvent and is curable during or after its application, and wherein the second layer is a fluid comprising liquid carrier different from the first solvent.

In accordance with another aspect of the invention, a method of applying an oral care agent to teeth includes applying the system to the teeth, whereby the first layer is at least partially cured before the second layer is applied.

In accordance with another aspect, a kit for applying the system includes a first composition including a matrix material, a first solvent, and an oral health care agent for forming a first layer; and a separate, second composition including a matrix material for forming a barrier layer which is less permeable to water than the first layer, said first composition being curable during or after its application and said second composition being a fluid comprising liquid carrier different from the first solvent.

The invention may take form in various components and arrangements of components, and in various process operations and arrangements of process operations. The drawings are only for the purpose of illustrating preferred embodiments and are not to be construed as limiting the invention.

FIG. 1 diagrammatically shows a system for applying an oral care agent in accordance with one embodiment disclosed herein.

FIG. 2 is a flow chart illustrating methods for using the exemplary composition, in accordance with embodiments disclosed herein.

FIG. 3 graphically illustrates the method of FIG. 2 in one embodiment.

Figure 1:
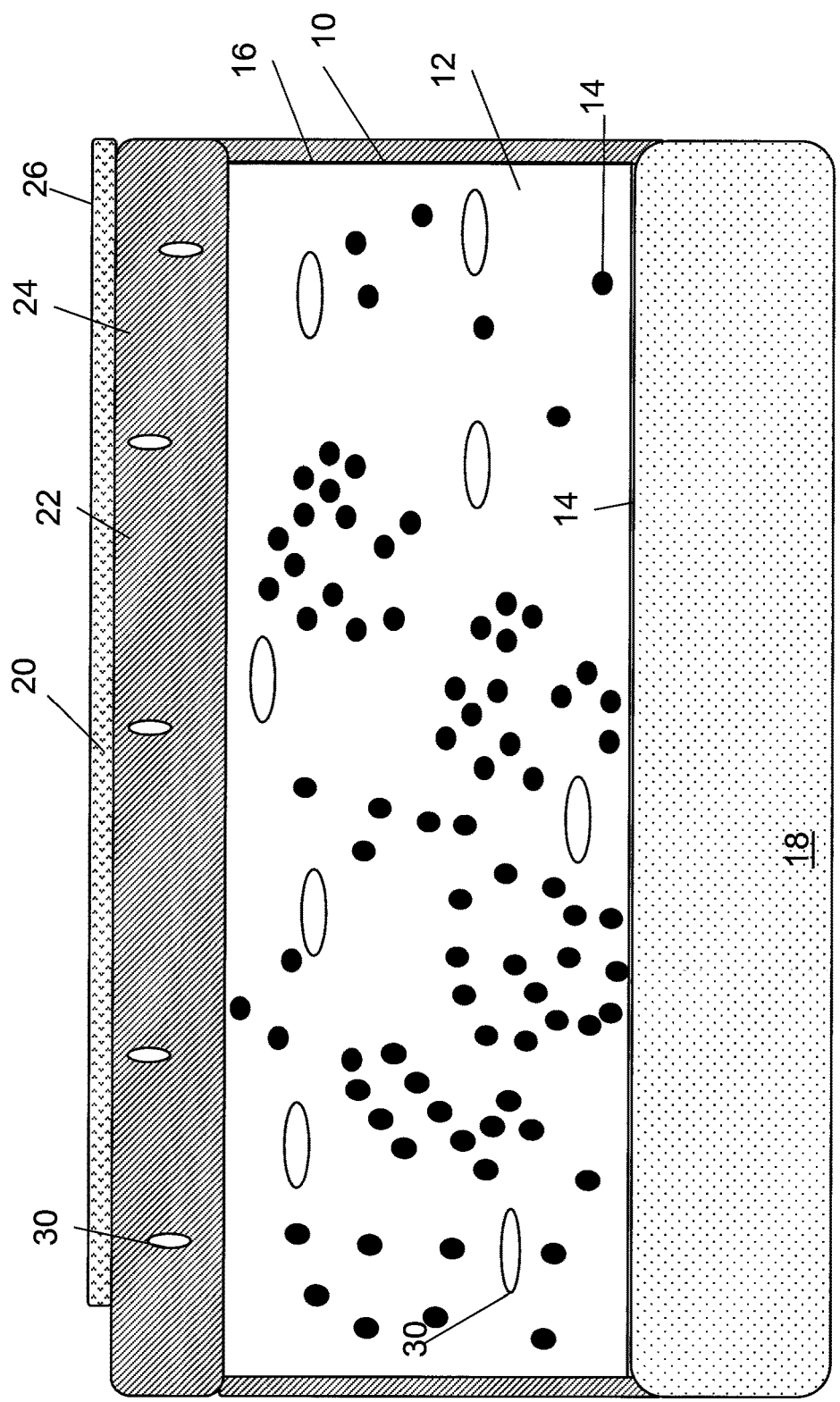

The layers as discussed in the context of this invention are essentially flowable during or after their application, and curable. Curing, also referred to as hardening or drying, refers to the phenomenon that the layers are applied as a flowable, typically liquid varnish. During or after their application, the flowability of at least the first layer, and preferably both layers, is reduced by curing, such as by solvent evaporation. Curing can also refer to the initiation, e.g. by means of photo-initiators, of crosslinking so as to increase the number of intermolecular bonds in the materials making up the layers.

The fluid, and preferably curable nature of the layers making up the system of the invention makes this system fundamentally different from other solutions that may exist in the art, whereby shaped devices such as a dental tray, sheet, strip, patch are applied.

The composition making up the second layer (i.e., the second composition) is a fluid comprising a liquid carrier different from the first solvent. The term "solvent" as used herein refers to a single solvent as to a mixture of solvents. Thus, the first solvent can consist of a single solvent, but it also can comprise a mixture of two or more solvents. The liquid carrier of the second composition can be a solvent, or a mixture of at least two solvents, but it can also be another liquid formulation, such as a melted wax. In the event that the liquid carrier of the second composition is a solvent or a mixture of solvents, the total solvent composition thereof is different from that of the solvent of the first composition.

Typically curable layers are those wherein the first layer comprises: a first polymer matrix; a first solvent; and the oral care agent; and wherein the second layer (20) comprises: a second polymer matrix (24); and a second solvent different from the first solvent. With reference to the meaning of the term solvent given hereinbefore, also the second solvent can be a single solvent or a mixture of solvent. In the event that both the first and second solvents are mixture, they can comprise the same solvents, but in different ratio's. Preferably, in the event of either or both of the solvents being a mixture, at least one solvent in such mixture for one layer, is not present in the solvent composition for the other layer. Preferably, the solvent compositions for both layers are fully different, i.e., not having a solvent in common.

In an interesting embodiment, the first layer is cured prior to the application of the second layer. If the curing is by a process other than solvent evaporation, e.g. by means of crosslinking, the second solvent can be (but does not need to be) the same as or similar to the first solvent. In the event that curing is by solvent evaporation it is preferred if the solvent in the second composition is sufficiently different from that in the first composition so as to prevent redissolution of the first layer.

Preferably, the aforementioned first layer, and preferably also the second layer, are such as to be curable during or after their application, by the at least partial evaporation of the solvents. This type of curing is hereinafter also described as "drying/curing" resulting in a layer that is "dried/cured".

In an alternative embodiment, the second layer can be a wax composition which would be rendered flowable by moderate heating (e.g. to a temperature of 35° C. to 50° C. before application, and which will then cure as a result of cooling. This embodiment is particularly interesting for the second layer. The wax composition could contain natural waxes such as paraffin wax or beeswax, mixed with oils or greases to obtain the desired harness, durability and removability.

In another alternative embodiment, the second layer could be a semi-solid composition such as petroleum jelly or grease which is not cured on the tooth and gradually erodes during usage.

The oral care agent delivery system of the present disclosure includes a first layer containing an oral care agent and a second layer which provides a protective and/or barrier function. The inclusion of the second layer enhances the delivery efficiency of the oral care agent by reducing the amount of oral care agent that leaks out of the first layer in unwanted directions. The first layer is the layer positioned generally closest to the tooth surface, and the second layer is substantially spaced from the tooth surface by the first layer (and optionally by one or more intermediate layers).

In addition to inhibiting the leaching of the oral care agent out of the first layer, the second layer may: be harder to prevent the first layer from washing away prematurely; be smoother than the first layer to prevent lip irritation and/or be more aesthetically pleasing; have more desirable color and/or reflectance properties; contain a component that activates the oral care agent in the first layer; contain pain relieving/numbing ingredients to reduce lip pain; and/or harden the first layer, thereby reducing cure time. The first and/or second layers may be subjected to pH adjustment. Color can be added by agent resistant dyes or particles. Either or both layers may contain flavorings, such as mint.

With reference to FIG. 1, a first composition 10, specifically, an oral care composition, in the form of a curable varnish, is shown. The first composition 10 includes a first matrix material 12 and an oral care agent 14 in solution or dispersed in the first matrix material 12. The first composition may further include a first solvent, when applied. The first solvent may be evaporated during a subsequent curing step, although a residual amount may remain. The first matrix material 12 includes a resin component. The resin component can include at least one of a polymerizable monomer and a film-forming polymer. The first composition is applied as a first layer 16 to teeth 18. The first layer 16 is bounded, on the side away from the teeth 18, by a second layer (i.e., a barrier layer) 20 formed from a moisture-resistant material, such as a polymer material. The barrier layer 20 is formed from a second composition 22, specifically, a barrier layer composition. The second composition 22 generally includes a second matrix material 24. The second composition 22 can be applied to the first layer in the form of a liquid, such as a solution including the second matrix material 24 in a second solvent. The second solvent may be evaporated during subsequent curing, although a residual amount may remain. In another embodiment the second composition is not configured to be dried/cured. For example, the second composition 22 may include one or more materials such as fats, lipids, oils, oleochemicals, and waxes which are generally insoluble in water. Non-limiting examples include monoolein, mineral oil, paraffin oil, olive oil, essential oils, oils derived from plants, paraffin wax, and glycerol. In some embodiments, the second composition includes a hydrophobic mixture or hydrocarbons, such as petroleum jelly. Hydrophobic polymers may be included in combination with these materials. Non-limiting examples of polymers than can be made hydrophobic and blended with these materials include polyesters, polyethers, polyolefins, polyvinyl acetates, polyamides, fluorinated polymers, silicone resins, styrene-based polymers, hydrocarbon polymers, block copolymers of polystyrene with polyalkylene and/or polydiene, and copolymers or mixtures thereof.

In some embodiments, the barrier layer may comprise first and second barrier layers 20, 26. For example, a third layer 26 may be applied over the second layer.

The first matrix material may be selected from poly(alkyl acrylates), poly(aryl acrylates), poly(alkyl methacrylates), poly(aryl methacrylates), poly(vinyl alcohol), poly(vinyl pyrrolidone), poly(ethylene glycol), poly(acrylic acid) derivatives, poly(acryl amide) derivatives, cellulose derivatives, and copolymers and mixtures thereof. Examples of suitable acrylates for forming the matrix material include alkyl acrylates, alkyl methacrylates, aryl acrylate, aryl methacrylates, methyl, ethyl, propyl, isopropyl, butyl, isobutyl, tert-butyl, phenyl, and benzyl esters of acrylic acid, methacrylic acid, ethacrylic acid, and butacrylic acid and combinations thereof. Example acrylates include methyl acrylate (MA), ethyl acrylate, methyl methacrylate (MMA), and ethyl methacrylate and combinations thereof.

In some embodiments, the first matrix includes one or more ester polymers of acetate.

In some embodiments, the first matrix material includes a mixture of a methyl methacrylate polymer and an ethyl acrylate polymer. Adding the ethyl acrylate to the methyl methacrylate softens the resulting composition. Without wishing to be bound by theory, it is believed that the softening results from the change from acidic to neutral pH in the mouth.

The first and second (and any additional) layers may be applied to the teeth one after the other, with any suitable applicator, such as a brush, wipe, fingers, dispensing device, a combination thereof, or the like.

The layers may be cured by evaporation (with or without heat and/or air drying), light curing (e.g., with UV light), moisture curing, a combination thereof, or the like.

The oral care agent 14 may be combined with other components of the first composition 10 and may be in the form of solid particles or a solution (e.g., an aqueous solution). The solution may contain at least 2 wt. %, or at least 5 wt. % or at least 10 wt. %, or at least 20 wt. %, or at least 30 wt. % of the oral care agent, and in some embodiments up to 50 wt. %, such as from 40-50 wt. %, of the oral care agent.

The oral care agent 14 (exclusive of water) may be present in the undried/uncured first layer at a concentration of at least 0.1 wt. %, or at least 1 wt. %, or at least 2 wt. % or at least 3 wt. %, or at least 5 wt. %, or at least 10 wt. %, and in some embodiments up to 95 wt. %, such up to 50 wt. %, or up to 40 wt. %, or up to 30 wt. %, or up to 20 wt. %.

The oral care agent 14 (exclusive of water) may be present in the dried/cured first layer at a concentration of at least 0.2 wt. %, or at least 1 wt. %, or at least 2 wt. %, or at least 5 wt. %, or at least 10 wt. %, or at least 20 wt. %, and in some embodiments up to 98 wt. %, such up to 60 wt. %, or up to 50 wt. %, or up to 40 wt. %, or up to 30 wt. %, or up to 20 wt. %.

A concentration of at least one oral care agent (e.g., all teeth whitening agents, or of peroxide-based whitening agents, in particular) in the first layer may be at least twice or at least 5 times a concentration by weight, of that oral care agent in the second layer. In some embodiments, the second layer is substantially free (e.g., contains less than 0.001 wt. %) of that oral care agent (e.g., of all teeth whitening agents, or of peroxide-based whitening agents, in particular).

In some embodiments, the oral care agent is/includes hydrogen peroxide or a precursor thereof, such as carbamide peroxide. The hydrogen peroxide (or its precursor) may be present in the first composition 10 in an amount sufficient to provide hydrogen peroxide in the uncured first layer at a concentration as specified above, and in one specific embodiment, in an amount equivalent to at least 0.1 wt. % and up to 25 wt. % hydrogen peroxide, prior to drying/curing, including from 1 wt. % to 20 wt. %.

The first and second layer solvents may be different to avoid intermixing of the layers. For example, the first solvent may be a polar solvent and the second solvent may be a non-polar solvent. Mixtures of solvents can be used as the first and second solvents. The first solvent may be a $C_2$-$C_{10}$ mono-alcohol or polyol, such as ethanol or propanol (e.g., isopropanol) or combination thereof. Exemplary second solvents have the general formula: $C_nH_{n+1}(CO_2)_xC_mH_{2m+1}$ where n and m are independently greater than or equal to 1 and smaller than 9, or smaller than 5, and n+m<12 or <8, and x=0 or 1. The second solvent may be, for example, a $C_4$-$C_{12}$ branched or unbranched alkane such as pentane, heptane, isoheptane, octane, isooctane, a $C_4$-$C_{12}$ branched or unbranched acetate, such as ethyl acetate, propylacetate, n-butyl acetate, isobutyl acetate, or amylacetate, a fluorinated solvent, cyclomethicone, and combinations thereof. In specific embodiments, the second solvent may be selected from the group consisting of heptane, pentane, ethyl acetate, and n-butyl acetate. The oral care agent may be soluble in the first solvent and insoluble (or less soluble) in the second solvent. The first matrix material 12 may be soluble in the first solvent and insoluble (or less soluble) in the second solvent. The second matrix material 24 may be soluble in the second solvent and insoluble (or less soluble) in the first solvent.

The first matrix material 12 may include a first polymer matrix component having a water diffusion coefficient in the range of from $10^{-9}$ to $10^{-6}$ cm$^2$/second. The second matrix material may include a second polymer matrix component having a water diffusion coefficient of less than $10^{-8}$ cm$^2$/second. A ratio of the first layer and second layer water diffusion coefficients may be at least 2:1 or at least 5:1. In some embodiments, the water diffusion coefficient of the first layer is at least 10 times greater than the water diffusion coefficient of the second layer. The water diffusion coefficient, as used herein, is given by $D=L^2/t$, where L is the dried/cured film thickness in centimeters and t is the desired application time in seconds for the varnish, such as 30 minutes (1800 sec).

The first polymer matrix material may be hydrophilic and the second polymer matrix material may be hydrophobic or at least less hydrophilic than the first polymer matrix material. The term hydrophobic, as employed herein, refers to an organic polymer which is substantially non-aqueous, having a water solubility of less than one gram per 100 grams of water at 25° C.

The first composition 10 and second composition 22 may each have a viscosity of at least 0.5 Pa·s or at least 1 Pa·s and up to 20.0 Pa·s, or up to 2.0 Pa·s, prior to any drying/curing that is performed.

The first polymer matrix material may be hydrophilic to enable water penetration. In contrast, the second polymer matrix material may be hydrophobic to inhibit water from passing through the second layer 20 into the first layer 16. In one embodiment, the first and second layers differ in at least one of chemical composition, water penetration, and viscosity.

The first polymer matrix material may be chosen from acrylic polymers, acrylate polymers, methacrylate polymers, ethyl methacrylate polymers, and copolymers and combinations thereof. For example, the first polymer matrix material may include one or both of a methyl methacrylate polymer and an ethyl methacrylate polymer. The methyl methacrylate polymer may have a higher glass transition temperature than the ethyl methacrylate polymer. The blending of these components may be selected to tailor the hardness and removability after the desired wear time, optionally with water ingression causing changes in the mechanical properties in time.

The second polymer matrix component may be chosen from acrylate polymers, methacrylate polymers, polyesters, polyethers, polyolefins, polyvinyl acetates, polyamides, fluorinated polymers, silicone resins, hydrocarbon polymers, polyvinylpyrrolidone-hydrogen peroxide complexes, styrene-based polymers, and copolymers and mixtures thereof. An exemplary polyvinyl acetate is an ethylene vinyl acetate copolymer.

An exemplary styrene-based polymer is a block copolymer including polystyrene end blocks. The mid-block(s) may include polyisoprene, polybutadiene, polyethylene-butylene, and/or poly(ethylene-propylene).

The compositions of the exemplary first layer and the second layer are incompatible/immiscible to inhibit inter-mixing.

In one embodiment, the compositions are in the form of a kit for use in forming a two layer oral care system for providing an oral care agent (14) to a tooth (18). The kit may include the first composition comprising a matrix material and an oral care agent (14) for forming a first of the layers and, a separate, second composition comprising a matrix material for forming a barrier layer which is less permeable to water than the first layer.

The kit may include, for example, first and second sealed packets, one for each of the first and second composites or first and second syringes.

The oral care agent 14 may include a whitening agent, a remineralizing agent, an anti-caries agent, an anti-plaque agent, an anti-odor agent, a fluoride agent, an anti-bacterial agent, a biofilm preventing or dispersing agent, a pH regulating agent, a long-term protective component, a reactive enzyme, a reactive radical, or combination thereof. Particular examples of these agents include:

Whitening Agents: The oral care agent may be/include a whitening (e.g., bleaching) agent. Example bleaching agents include hydrogen peroxide, carbamide peroxide and other hydrogen peroxide complexes, alkali metal percarbonates, perborates, such as sodium perborate, persulfates, such as potassium persulfate, calcium peroxide, zinc peroxide, magnesium peroxide, strontium peroxide, peroxyacids, sodium chlorite, combinations thereof, and the like. The term "bleaching agent," herein refers to compounds which are themselves bleaches and to compounds which are bleach precursors, such as carbamide peroxide, which react or decompose to form a bleach, such as hydrogen peroxide. The bleaching agents can be solid or liquid at ambient conditions. Liquid bleaching agents include peroxides such as hydrogen peroxide, which may be introduced to the first composition 10 as an aqueous solution. Solid bleaching agents include carbamide peroxide, which is an adduct (or stable mixture) of urea and hydrogen peroxide ($CH_4N_2O$—$H_2O_2$). The material is a white, crystalline solid that dissolves in water to release the two components from which it is formed. Carbamide peroxide contains the equivalent of 36.1 wt. % hydrogen peroxide. For example, a varnish composition containing 16.6 wt. % carbamide peroxide can release 5.9 wt. % hydrogen peroxide. Solid bleaching agents can be introduced in the form of particles, which may be encapsulated. Encapsulated carbamide peroxide particles may be used, as disclosed for example, in U.S. Provisional Application Ser. No. 61/604,079, filed Feb. 28, 2012.

In an interesting embodiment related to whitening, the layers are subjected to pH adjustment. In particular, the first layer thereby comprises two phases (A containing peroxide at low pH, e.g. pH 3-5.5, particularly pH 4 to pH 5, and more particularly pH 4.5, and B containing an alkali, e.g. KOH at pH>8) which are mixed at the point of use to give a final pH of 5-8 on the tooth. A pH adjustment can be desirable to optimize stability and product life (low acidic pH) while avoiding enamel degradation (higher pH).

Tartar control (anticalculus) agents: these may include phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts, and mixtures thereof.

Fluoride ion sources: These may be useful, for example, as an anti-caries agent. Orally acceptable fluoride ion source which can be used include potassium, sodium and ammonium fluorides and monofluorophosphates, stannous fluoride, indium fluoride and mixtures thereof.

Tooth and soft tissue desensitizers: these may include stannous ions, such as halides and carboxylate salts, arginine, potassium citrate, potassium chloride, potassium tartrate, potassium bicarbonate, potassium oxalate, potassium nitrate, strontium salts, and mixtures thereof.

Antimicrobial (e.g., antibacterial) agents: these may include orally acceptable antimicrobial agents, such as Triclosan (5-chloro-2-(2,4-dichlorophenoxy)phenol); 8-hydroxyquinoline and salts thereof, zinc and stannous ion sources such as zinc citrate; copper (II) compounds such as copper (II) chloride, fluoride, sulfate and hydroxide; phthalic acid and salts thereof such as magnesium monopotassium phthalate; sanguinarine; quaternary ammonium compounds, such as alkylpyridinium chlorides (e.g., cetylpyridinium chloride (CPC), combinations of CPC with zinc and/or enzymes, tetradecylpyridinium chloride, and N-tetradecyl-4-ethylpyridinium chloride); bisguanides, such as chlorhexidine digluconate; halogenated bisphenolic compounds, such as 2,2' methylenebis-(4-chloro-6-bromophenol); benzalkonium chloride; salicylanilide, domiphen bromide; iodine; sulfonamides; bisbiguanides; phenolics; piperidino derivatives such as delmopinol and octapinol; *magnolia* extract; grapeseed extract; thymol; eugenol; menthol; geraniol; carvacrol; citral; eucalyptol; catechol; 4-allylcatechol; hexyl resorcinol; methyl salicylate; antibiotics such as augmentin, amoxicillin, tetracycline, doxycycline, minocycline, metronidazole, neomycin, kanamycin and clindamycin; and mixtures thereof. Other useful antimicrobials are disclosed in U.S. Pat. No. 5,776,435.

Antioxidants: orally acceptable antioxidants which can be used include butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

Antiplaque (e.g., plaque disrupting) agent: orally acceptable antiplaque agents can include stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates, and mixtures thereof.

Anti-caries agents: examples of these include calcium glycerylphosphate and sodium trimetaphosphate.

Anti-inflammatory agents: orally acceptable anti-inflammatory agents can include steroidal agents, such as flucinolone and hydrocortisone, and nonsteroidal agents (NSAIDs) such as ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone, phenylbutazone, and mixtures thereof.

$H_2$ antagonists: antagonists useful herein include cimetidine, etintidine, ranitidine, ICIA-5165, tiotidine, ORF-17578, lupititidine, donetidine, famotidine, roxatidine, pifatidine, lamtidine, BL-6548, BMY-25271, zaltidine, nizatidine, mifentidine, BMY-52368, SKF-94482, BL-6341A, ICI-162846, ramixotidine, Wy-45727, SR-58042, BMY-25405, loxtidine, DA-4634, bisfentidine, sufotidine, ebrotidine, HE-30-256, D-16637, FRG-8813, FRG-8701, impromidine, L-643728, HB-408.4, and mixtures thereof.

Nutrients: Suitable nutrients include vitamins, minerals, amino acids, proteins, and mixtures thereof.

The oral care agent 14 (e.g., whitening agent) may be present in the undried/uncured first layer at from 0.1 wt. % to 50 wt. %. In one embodiment, the oral care agent may be present at from 2 wt. % to 25 wt. % of the composition 10, or when formulated for other use, the composition may be from 2 wt. % to 8 wt. % equivalent of hydrogen peroxide. The oral care agent may be heterogeneously or homogeneously dispersed in the matrix material. In some embodiments, the concentration of oral care agent is higher near the teeth 18.

In one embodiment, the oral care agent 14 (e.g., whitening agent) is present in the core of encapsulated particles. The core is encapsulated in a shell formed of a carrier material. The carrier material can be formed of any suitable material, which is different, at least in some respects, from that of the core, to space oral care agent from the matrix material 12 and/or to modify the rate of release of oral care agent from the composition, and can be a solid at ambient temperature. In other embodiments, the oral care agent is not encapsulated.

The carrier material forming the shell may include a hydrophobic material and optionally a release rate modifier in contact with, e.g., dispersed in, the hydrophobic material. In other embodiments the hydrophobic material and release rate modifier may form two distinct layers, with the hydrophobic material forming the outermost layer. The microencapsulation may serve to control release of the oral care agent from the core and/or to separate the oral care agent from other chemicals in the varnish with which it might react. In some embodiments, the matrix material can provide for slow release of the oral care agents and the microencapsulation simply the separation, in which case, the shell may provide a quick release from the particles. In other embodiments, the shell provides for slow release of the oral care agents.

In addition to the oral care agent 14 and the matrix 12, the first layer 16 and/or the second layer 20 may further include other particles 30 which serve as viscosity modifiers, such as silica particles, which are dispersed in the resin component of the matrix material 12. Other viscosity modifiers may be used. Other optional additives which may be present in the second layer 20 include tartar control (anticalculus) agents, abrasives, fluoride ion sources, remineralization agents tooth desensitizers, anticaries agents, antimicrobial agents, antioxidants, anti-plaque agents, anti-inflammatory agents, coloring agents, such as titanium dioxide, flavoring agents, coloring agents, dyes, particles, and the like. These additives may each be present in one or more of the first layer 16 and the barrier layer 20. The additives contained in the first layer 16 and the barrier layer 20 may be the same or different and may be present in the same or different concentrations. In particular, whitening agents are present at lower concentrations or are absent from the second layer.

Remineralization agents can also be self-assembling peptides, e.g., as known from P A Brunton et al., in British Dental Journal 215, E6 (2013). This particularly concerns monomers (particularly amino acids) or short chain polypeptides, proteins or short chain collagens, with an affinity for the tooth surface and with the ability to nucleate hydroxyapatite crystallisation. Suitable proteins other than collagen include, e.g., include proteins present in developing the extracellular matrix of enamel, such as amelogenin, ameloblastin, enamelin, amelotin, glycans. These are also known to have a self-assembly property, and are present in enamel, where the remineralisation primarily takes place.

In embodiments wherein the oral care agent particles 14 are encapsulated, the additives may be included in the shell and/or the core of the particles, as appropriate.

To evaluate candidate compositions for durability and removal, samples of the composition can be applied to teeth, such as bovine teeth, tested to see if they cure sufficiently to retain their integrity for a few minutes or hours, for example, and can be removed by brushing.

As will be appreciated, FIG. 1 is intended to be illustrative only and is not intended to be to scale.

One or both of the first layer 16 and the second layer 20 may be applied by brushing, spraying, or with a wipe.

The two compositions 10, 22, when applied on the teeth, may be allowed to cure or in some embodiments at least one of heat, an air jet, and light may be applied to speed up the process. Lip refraction may be used to keep the lips from coming into contact with the compositions as they cure. Curing is used herein to describe any process by which the composition forms an intact layer on the teeth which is capable of remaining on the teeth throughout the whitening process. Vibration may be used during curing to improve the smoothness of the layer. Soft tissue in the mouth, such as the gums, may be protected, prior to applying the compositions 10, 22 with a layer of a suitable material (e.g., a soft and smooth material). Different methods may be used for applying the two layers.

Method of Using the System

The first composition 10 and barrier layer composition 22 may be applied to the teeth 18 of a person, to provide oral care, e.g., to treat (e.g., whiten) the teeth.

Figure 2:
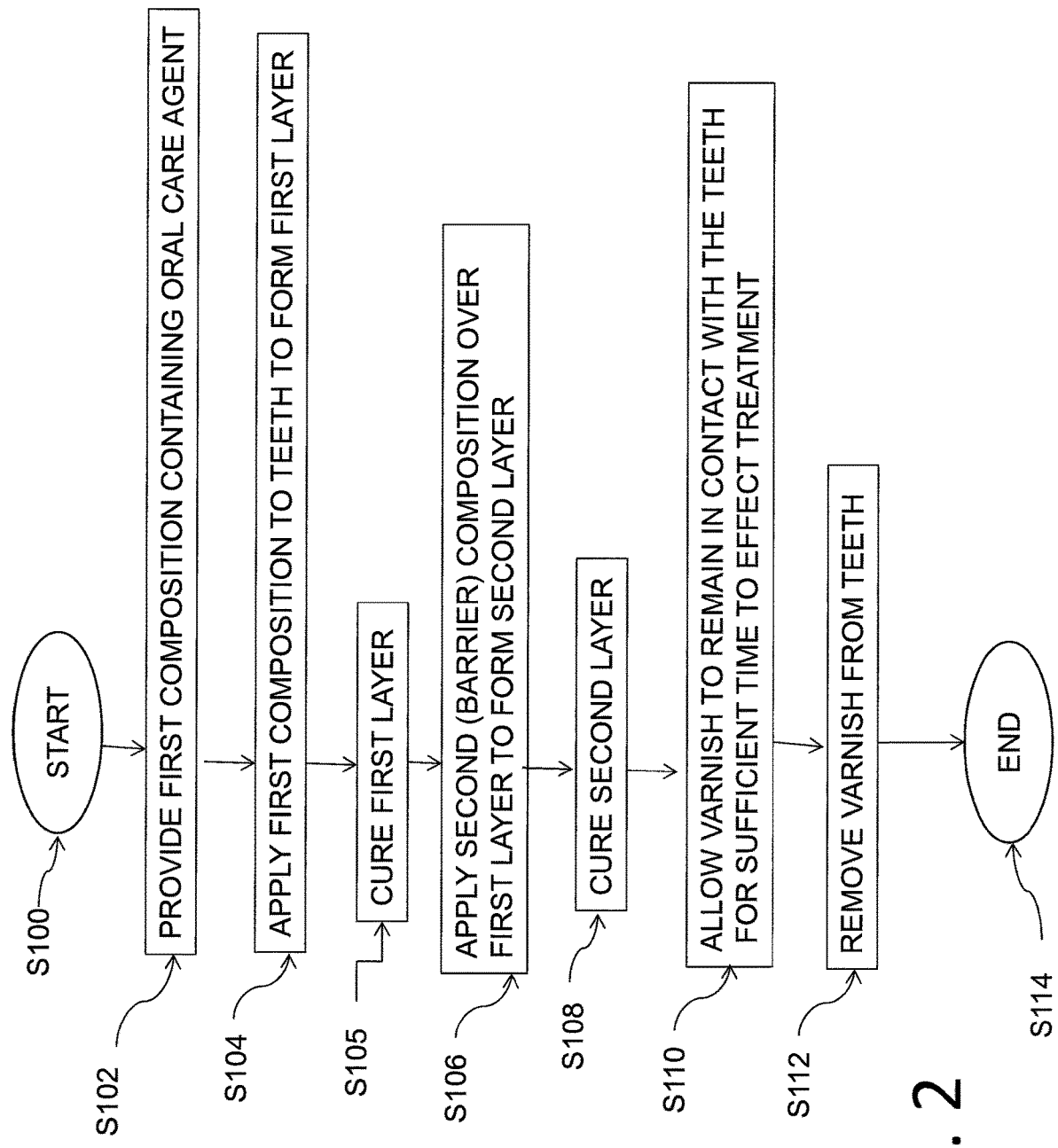
Figure 3:
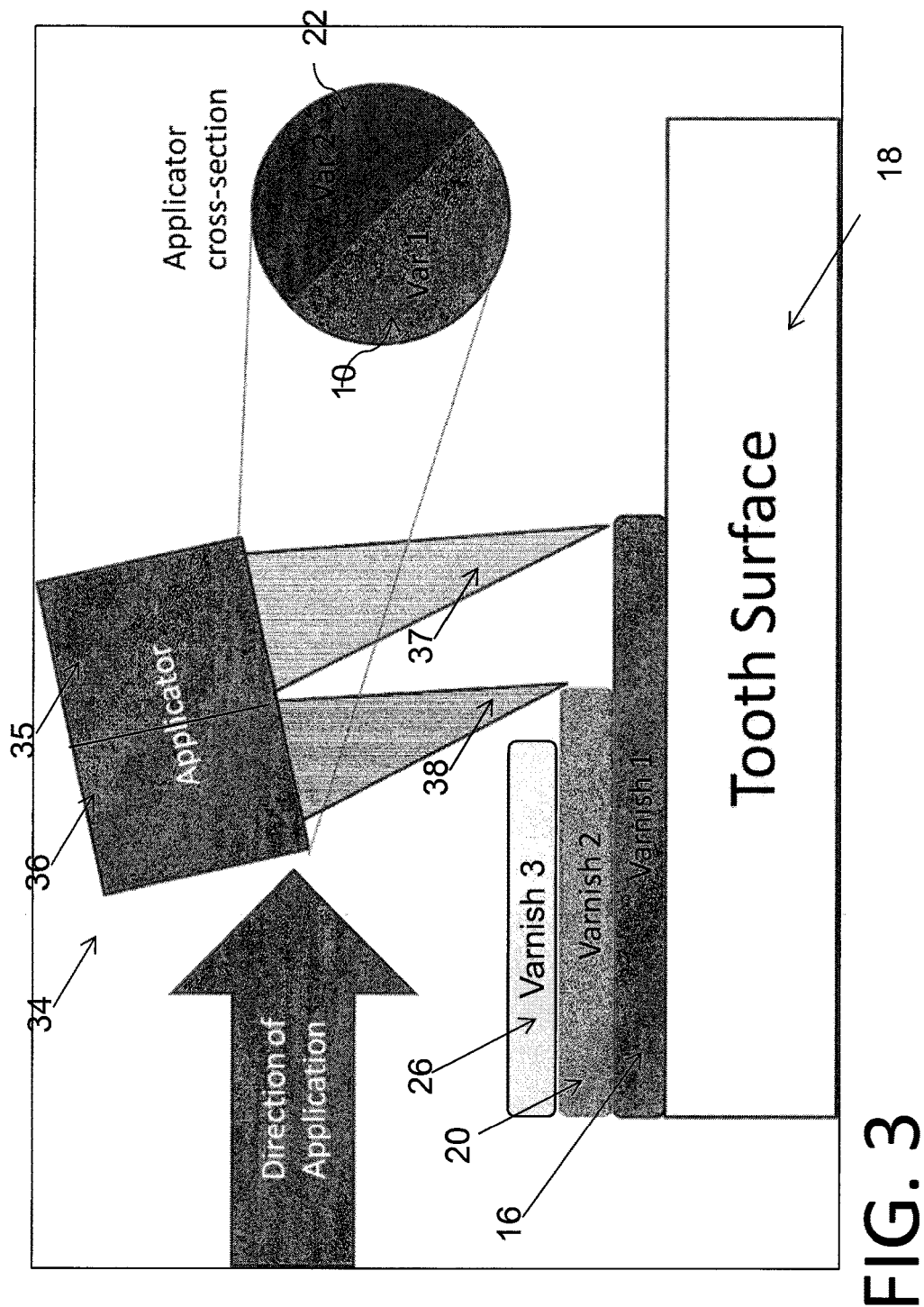

With reference to FIGS. 2 and 3, a method for treating teeth with the compositions is illustrated. The method begins at S100. At S102, the first composition 10 is provided.

At S104 the first composition is applied to the teeth of a person or animal to be treated. The composition may be applied by a dental professional, such as a dentist, or by the wearer. For example, the first composition 10 may be applied to the teeth using an applicator, such as a pen, brush, piece of foam, cloth applicator, dental tray, or to two-compartment syringe to form the first layer. In other embodiments, the first composition 10 may be inserted into an applicator, such as into the dental tray, which is positioned adjacent the teeth and then removed, for example, after partial drying/curing of the composition.

The first composition 10 may be applied to the teeth at a thickness t of for example, from 50-500 µm, such as from 50-300 µm, e.g., about 200 µm. In the some embodiments wherein the oral care agent is present in the form of particles, the film is greater in thickness than the average diameter of the particle, for example, at least twice or at least three times the average diameter of the particles. This allows the varnish to be smooth to the touch, when cured.

At S105, the composition 10 may be dried and/or cured. Curing the composition 10 may reduce the thickness of the first layer, particularly if a solvent is present in the applied composition 10. The curing/hardening may be performed with light, air, moisture, solvent evaporation, or a combination of these. In one embodiment, the matrix material 12 includes a resin component which is moisture-cured, for example, by saliva naturally present on the teeth. In another embodiment, the matrix material includes a solvent which evaporates. In yet another embodiment, the resin component of the matrix material includes a curing agent and is cured by light, such as blue light, from a suitably positioned light source. Different compositions for these types of matrix material are discussed below. In one embodiment, the exemplary composition dries/cures rapidly, for example in 10 minutes or less, such as in under three minutes, for example, from a few seconds to a minute. For compositions which take minutes or longer to dry/cure, soft tissue in the mouth, such as the lips and/or gums, may be protected with a coating or held away from the teeth, e.g., with a lip retractor. The cured first layer may have a thickness from 20-200 µm, such as from 50-100 µm.

At S106, a barrier layer 20 is applied over the first layer 16 of composition 10.

At S108, the second layer 20 may be cured or otherwise hardened to form a barrier film. The barrier film serves a protective function for the firm layer.

In one embodiment, the source of light in wavelengths suitable for drying/curing the composition, such as blue light, is positioned adjacent the first layer 16 and second layer 20. The light of the specified wavelength range may be applied by a light source integral with the applicator 34, if used, or by a separate light source.

In some embodiments, S105 is not performed prior to application of the second layer 20. Barrier layer 20 may be cured contemporaneously with the composition 10.

The two layers remain in position on the teeth for a selected treatment time (S110).

At S112, after sufficient time to effect treatment with the oral care agent, the first layer of varnish 16 and the second layer 20 are removed. For example, at the end of the treatment period, the layers are removed from the teeth by peeling them away from the teeth and/or by brushing the teeth. The process may be repeated, for example, once a day, week, or month more or less frequently. The method ends at S114.

FIG. 3 illustrates an exemplary applicator 34 in the form of a double barreled syringe which can be used to apply the composition 10 in one embodiment. The applicator includes first and second chambers 35, 36 which hold the first and second compositions separate from each other. A first outlet 37 delivers the first composition 10 on to the teeth to form the first layer 16 and a second outlet 38, downstream of the first outlet (in the direction of movement), delivers the second composition 22 on to the teeth for forming the second layer 20. One or more teeth can be treated in a single application. The applicator may also include a fan (not shown) to reduce curing time. As will be appreciated, two separate applicators may alternatively be used, one for each layer.

In teeth whitening applications, the time can be a sufficient time to effect at least a partial whitening of the teeth, e.g., a change in color of at least 1 ΔE. For example, at the end of the treatment period, the composition 10 is removed from the teeth by peeling it away from the teeth and/or by brushing the teeth. The process may be repeated, for example, once a day, week, or month or less frequently, until a desired color change is effected or to maintain whiteness of the teeth.

ΔE is computed according to the CIE76 definition, using the L*,a,*b* values of the teeth (which may be averaged values), before whitening (denoted by the subscript 1) and after whitening (denoted by the subscript 2), according to the formula:

$$\Delta E = \sqrt{(L^*_2 - L^*_1)^2 + (a^*_2 - a^*_1)^2 + (b^*_2 - b^*_1)^2}.$$

The matrix material 12 is formulated to form a film on the teeth which retains the oral care agent in close proximity to the surface of the teeth. Over a period of from about 30 minutes to several days, such as from 2-10 hours, the oral care agent 14 may be activated by moisture.

Exemplary First Varnish Compositions

Suitable varnish compositions 10 include self-cured and light-cured compositions.

Example compositions 10 may include (the components totaling 100%):

A. 2-95 wt. % (or at least 3 wt. %, or at least 5 wt. %, or at least 10 wt., and in some embodiments, up to 80 wt. % or up to 50 wt. % or up to 20 wt. %) of oral care agent 14 (exclusive of water);

B. 98-2 wt. % (or 10-95 wt. %, or 80-20 wt. %) of the matrix material 12, the matrix material consisting of (the matrix material components totaling 100%):

B1. 1-70 wt. % (or 5-50 wt. %, or 10-20 wt. %) of a first polymer matrix component, which may comprise at least one of a polymerizable monomer and the reaction product of a polymerizable monomer and a curing agent, B2. 0-50 wt. % (or 2-30 wt. %, or 5-10 wt. %) of a first solvent, B3. 0-40 wt. % viscosity modifier;

B4. 0-50 wt. % (or 1-20 wt. %) other additives (i.e., other than the components A, B1, B2, and B3), such as one or more of particles, colorants, anti-tartar agents, anti-caries agents, surfactants, antimicrobial agents, anti-oxidants, anti-plaque agents, and the like, and C. 0-30 wt. % water.

In some embodiments, the matrix material 12 can be substantially free of water (includes less than 5 wt. % water, or less than 1 wt. % water). In some embodiments, no water is used in forming the composition. Additionally, the components used in forming the composition may be dry, and may be anhydrous. In other embodiments, the oral care agent is in aqueous solution and the first layer includes water derived at least in part from the aqueous solution. For example, the first composition 10 may be at least 0.1 wt. % water, or at least 1 wt. %, or at least 5 wt. % water and may be up to 30 wt. % water, or up to 20 wt. % water.

A ratio, expressed by weight, of oral care agent to the matrix material in the composition 10 can range from 1:50 to 50:1, such as at least 1:10 (or at least 1:2, or at least 1:1, or at least 5:1, or at least 10:1, or at least 15:1).

The first polymer matrix component B1 can include one or more polymerizable monomers and a curing agent. In some embodiments, the first polymer matrix component B1 can include a film forming polymer and/or resin. A "monomer," as used herein includes polymerizable monomers, dimers, and oligomers, except as noted.

The first solvent B2 can be any compatible pharmaceutically-acceptable organic solvent, such as an alcohol, unsaturated hydrocarbon, ketone, or the like, which is liquid and/or volatile at ambient temperatures (20-30° C.).

The viscosity modifier may include one or more of particles 30, waxes, gums, and other thickeners, and.

Example matrix compositions are now described.

1. Self-cure compositions: these include moisture cured varnishes and solvent based varnishes.

a. Moisture Cured Varnishes:

Examples of these include varnishes based on natural resins, such as colophonium resin which cures when in contact with saliva. Varnishes of this type are disclosed for example, in WO2009/124311. Shellac may also be used in such compositions, alone or in combination with another resin. An example moisture-cured matrix material B suited to use in such varnishes 10 may include (totaling 100%):

B1. 1-70 wt. % (or 5-50 wt. %, or 10-20 wt. %) of a first polymer matrix component (moisture-cured and/or air-cured), B2. 1-30 wt. % (or 2-20 wt. %, or 5-10 wt. %) of a first solvent, B3. 0-40 wt. % viscosity modifiers (or 1-20 wt. %, or 5-10 wt. %), such as one or more of:

B3a. particles 30 (e.g., at 1-20 wt. %, or 5-10 wt. %),
B3b. waxes (e.g., 1-20 wt. %, or 5-10 wt. %), and
B3b. gums (e.g., 1-20 wt. %, or 5-10 wt.), and
B4. 0-20% (or 1-20%) of other additives.

The composition 10 containing such a matrix material is applied on damp teeth and the mouth closed to allow saliva to cure the resin.

As an example, a matrix composition 12 can be formed from colophonium resin and/or shellac, a first solvent, and optionally one or more waxes and/or gums. Example first solvents include $C_1$-$C_{20}$ alcohols and ketones, e.g., ethanol, propanol, cetyl alcohol, stearyl alcohol, and $C_6$-$C_{20}$ hydrocarbons, such as hexane. Example hydrocarbon waxes include esters of fatty acids and long chain alcohols that are solid or viscous liquids at room temperature. These include naturally occurring waxes such as beeswax, and $C_{40}$-$C_{100}$ alkanes and fatty acid esters. Gums, such as mastic (a resin obtained from *Pistacia lentiscus* Var. *Chia*) may be included in the matrix material.

One example moisture-curable composition 10 includes a matrix material 12 comprising colophonium resin and an organic solvent (e.g., one or more of ethanol, methanol, n-hexane, and cetostearyl alcohol), and the oral care agent 14.

Another example moisture-curable composition 10 includes a matrix material 12 comprising shellac, colophonium resin, a solvent (such as ethanol), beeswax, and mastic, and the oral care agent 14.

b. Solvent-based varnishes: these are based on solvent evaporation. An exemplary matrix material of this type can include a conventional polyacrylic acid based polymer in combination with a solvent, such as $C_1$-$C_{10}$ mono-alcohol or polyol, e.g., one or more of methanol, ethanol, and glycerol, and optionally a buffer agent. The polyacrylic acid-based polymer may include functional groups which increase the permeability of the polymer matrix component to water, such as ammonium groups, e.g., as their salts.

As an example, the matrix material can be formed from acrylic acid polymers such as a Carbomer, optionally a surfactant such as a polysorbate or sorbitan ester (e.g., sorbitan monooleate), glycerol, and EDTA as buffering agent. Other components may be present, such as arginine and potassium nitrate.

A composition 10 containing such a resin can be applied on dry teeth and the mouth kept open to allow the resin to cure in 30 seconds to 2 minutes.

An example solvent-based matrix material B may include (totaling 100%):

B1. 20-70 wt. % (or at least 25 wt. %, or at least 30 wt. %, and in some embodiments up to 65 wt. %, or up to 60 wt. %) of first polymer matrix component, B2. 1-30 wt. % (or at least 2 wt. %, or at least 5 wt. % and in some embodiments up to 20 wt. % or up to 10 wt. %) of a first solvent, B3. 0-40 wt. % viscosity modifiers, such as particles 30, waxes, and/or gums, and B4. 0-20% other additives, such as 0.001-5 wt. % of a surfactant and 0.001-5 wt. % of a buffering agent.

In one embodiment, the solvent based varnish may include, in the above amounts:

B1. B1i. Copolymer derived from esters of acrylic and methacrylic acid, e.g., available under the tradename Eudragit® from Evonik (e.g., Eudragit® RL PO, a poly (ethyl acrylate-co-methyl methacrylate-co-trimethylammonioethyl methacrylate chloride), which is a copolymer of ethyl acrylate, methyl methacrylate and a low content of methacrylic acid ester (ratio of 1:2:0.2) with quaternary ammonium groups, which are present as their salts. The polymer has the general formula:

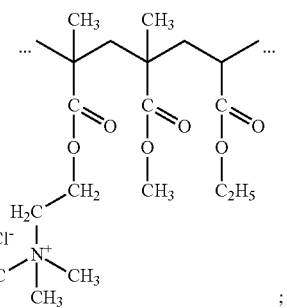

and/or

B1ii. Anionic copolymer based on methacrylic acid and ethyl acrylate, e.g., available under the tradename Eudragit® L 100-55 (a poly(methacrylic acid-co-ethyl acrylate) 1:1). The polymer has the general formula:

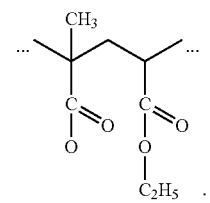

The ratio of RL PO to L 100-55 may be in the range of from 5:1 to 2:1, including 4:1.

B2. Solvent such as ethanol

B4. Other additives (optional) to increase efficiency, product delivery, product shelf life and wearer suitability, such as:

Stabilizer such as polyphosphates, benzoic acid, salicyclic acid, EDTA, sodium perborate Saliva inhibitor such as sodium fluoride Flavoring, such as mint or peppermint oil Emulsifier, such as Tween 20, Span 80

Humectant, such as glycerin, sorbitol, xylitol, PEG pH control agent, such as sodium bicarbonate, sodium hydroxide, citric acid This matrix material is combined with the oral care agent.

2. Light-cure varnishes: In the case of light-cured compositions, the resin component B1 may comprise one or more polymerizable monomers B1a, B1b and optionally one or more curing agents B1c, B1d. Example polymerizable monomers may include one or more functional monomers B1a and optionally a crosslinking monomer B1b. The curing agent may include at least one of a photoinitiator B1c and a co-initiator B1d.

An example light-curable matrix material B may include (totaling 100%):

B1. 1-70 wt. % (or at least 5 wt. %, or at least 10 wt. %, and in some embodiments, up to 50 wt. %, or up to 20 wt. %) of first polymer matrix component, B2. 1-30 wt. % (or at least 2 wt. %, or at least 5 wt. %, and in some embodiments, up to 20 wt. %, or up to 10 wt. %) of a first solvent, B3. 0-40 wt. % viscosity modifying particles 30 and/or waxes, and B4. 0-20% other additives.

An example light-curable first polymer matrix component B1 may include (totaling 100%):

B1a. Functional monomer (e.g., HEMA): 10-50 wt. %

B1b. Crosslinking monomer (e.g., Bis-GMA): 50-90 wt. %

B1c. Initiator (e.g., Camphorquinone): 0.1-2 wt. %

B1d. Co-initiator (e.g., DMAEMA) 0-3 wt. %, e.g., at least 1 wt. %.

B1e. Inhibitor (to reduce self-polymerization in storage) 0-3 wt. %, e.g., at least 0.01 wt. %, such as about 0.1%.

Suitable functional monomers B1a include monofunctional and multifunctional acrylates and methacrylates (referred to jointly herein as (meth)acrylates). Suitable (meth)acrylates include those having a viscosity of about 0.1 to about 100 cps at 25° C. Use of multifunctional (meth)acrylates can increase cure speed of the resin composition. Examples of these monomers include hydroxyalkyl methacrylates, such as 2-hydroxyethyl methacrylate (HEMA) and 2-hydroxypropyl methacrylate; ethylene glycol methacrylates, including ethylene glycol methacrylate, diethylene glycol methacrylate, tri(ethylene glycol) dimethacrylate and tetra(ethylene glycol) dimethacrylate; and diol dimethacrylates such as butanedimethacrylate, dodecanedimethacrylate, and 1,6-hexanedioldimethacrylate (HDDMA), and mixtures of these.

Suitable crosslinking monomers B1b include bisphenol glycerolate dimethacrylate (Bis-GMA), which is the condensation product of bisphenol A and glycidyl methacrylate; triethylene glycol dimethacrylate (TEDGMA); aliphatic and aromatic polyurethane dimethacrylate (PUDMA); and urethane dimethacrylate (UDMA), and mixtures of these. Other viscous resins having a viscosity of greater than about 1000 centipoise (cps) at 60° C. can also be used. The amount of crosslinking monomer can have an influence on mechanical property and viscosity of the resin.

Other examples of suitable (meth)acrylates include higher viscosity (meth)acrylates, such as aliphatic and aromatic diurethane dimethacrylates (DUDMA), polycarbonate dimethacrylate (PCDMA), a condensation products of two parts of a hydroxyalkylmethacrylate and 1 part of a bis (chloroformate), as disclosed in U.S. Pat. Nos. 5,276,068 and 5,444,104; and ethoxylated bisphenol A dimethacrylate (EBPDMA), as disclosed in U.S. Pat. No. 6,013,694.

Most methacrylates are moderately hydrophobic. Some form films which are very strong and do not release easily from the teeth. In some embodiments, a first (meth)acrylate B1a, which forms strong bonds with teeth is combined with a second (meth)acrylate B1b, e.g., a dimer, as a crosslinker which forms less strong bonds. As an example, HEMA (hydroxyethyl methacrylate), which is semi-soluble in water, is combined with a less-strong dimer, such as polyethylene glycol (PEG) dimethacrylate (a polymer of ethylene oxide which is terminated at each end by a methacrylate unit). The molecular weight of the PEG can be controlled/chosen to achieve the desired bonding and release properties. This gives cross linking with a weaker backbone and moderate hydrophilicity. As an example, the PEG dimethacrylate can have a number average molecular weight of 100-2000, such as at least 500. Additionally or alternatively, by modifying the stoichiometry, e.g., by overloading the blend with HEMA, the crosslink density can be controlled.

Example photoinitiators B1c include camphoroquinone (CQ), phenylpropanedione (PPD), benzoin esters, benzophenone, acylphosphine oxides, and lucirin. A co-initiator B1c may be used in combination with the photoinitiator, such as a tertiary aliphatic amine, e.g., dimethylaminoethylmethacrylate (DMAEMA).

Suitable co-initiators B1d. include DMAEMA, and aliphatic and aromatic amines (e.g., in the case of CQ as an intiator).

Suitable inhibitors B1e. include butylated hydroxytoluene, butylhydroxytoluene (BHT), monomethyl ether hydroquinone (MEHQ).

Exemplary solvents B2 for such resins include $C_2$-$C_{20}$ alcohols e.g., ethanol, propanol, cetyl alcohol, stearyl alcohol, $C_3$-$C_{20}$ ketones, such as acetone, and $C_6$-$C_{20}$ hydrocarbons, such as hexane and heptane.

Such formulations may be cured with blue light, or other wavelengths in the visible range. Suitable light absorption/curing is from 400-490 nm, such as from 475-480 nm (depending on the actual formulation). As an example, CQ is a photo initiator which absorbs with a peak in the blue wavelength range and produces radicals when excited in the 460-490 nm range. Co-initiators, such as DMAEMA, accelerate the light-cure process. When formulated as a composition 10 and applied to dry teeth, the composition may cure in 10 seconds to 1 minute under blue light illumination. PPD uses a shorter wavelength (420-430 nm).

As one example, a mixture of acrylic acid, Bis-GMA, CQ, HEMA and optionally DMAEMA is combined with a solvent, such as acetone and/or ethanol, the exemplary particles and optionally silica particles. The composition can cure in 30 seconds under blue light. Such a composition stays intact in excess saliva, and can be completely removed by peeling and brushing.

As another example, a mixture of acrylic acid, itaconic acid, and HEMA is combined with calcium glycerophosphate, Bis-GMA, camphoroquinone, silica beads, and the exemplary particles and applied to the teeth. The composition can cure in 10 to 20 seconds under blue light.

Viscosity Modifiers (B3)

The exemplary composition 10 may include at least 1 wt. % (or at least 2 wt. %, or at least 5 wt. %, or at least 10 wt. %, or at least 15 wt. %) of component B3, such as up to 50 wt. %, or up to 20 wt. %.

Component B3 of the composition 10 disclosed herein may include from 0-100 wt. %, e.g., at least 5 wt. % (or at least 20 wt. %, or at least 40 wt. %) of particles 30. The particles may have a Mohs hardness of at least 2 (or at least 3, or at least 5).

Particles 30 may serve as viscosity modifiers and/or abrasives. An abrasive may be useful, for example, as a polishing agent. Suitable particles include silica, for example in the form of silica gel, hydrated silica or precipitated silica, alumina, insoluble phosphates, orthophosphates, polymetaphosphates, and beta calcium pyrophosphate, calcium carbonate, resinous abrasives such as urea-formaldehyde condensation products and mixtures thereof.

Suitable waxes and gums useful as viscosity modifiers include those mentioned elsewhere herein.

Suitable thickeners useful as viscosity modifiers may include starches, anionic polymers, and the like.

Other Additives (B4)

The composition 10 may include at least 1 wt. % (or at least 2 wt. %, or at least 5 wt. %, or at least 10 wt. %, or at least 15 wt. %) of component B4, such as up to 50 wt. %, or up to 20 wt. %.

As examples of other additives, the composition 10 may include one or more of the following:

Colorants: The colorant may be selected to provide the film with a white appearance or a tint.

Tooth and soft tissue desensitizers: these may include stannous ions, such as halides and carboxylate salts, arginine, potassium citrate, potassium chloride, potassium tartrate, potassium bicarbonate, potassium oxalate, potassium nitrate, strontium salts, and mixtures thereof.

Anti-staining agents: such as silicone polymers.

Flavoring agents: any of the flavoring agents commonly used in toothpastes may be used, by way of example.

Exemplary Second Varnish Compositions

Suitable varnish compositions for the barrier layer include self-cured and light-cured compositions.

Example compositions may include (the components totaling 100%):

A. 1-70 wt. % (or at least 5 wt. %, or at least 10 wt. %, and in some embodiments, up to 50 wt. %, or up to 20 wt. %) of a second polymer matrix component, which may comprise at least one of a polymerizable monomer and the reaction product of a polymerizable monomer and a curing agent, B. 1-98 wt. % (or at least 5 wt. %, or at least 10 wt. %, or at least 50 wt. %, or at least 60 wt. %, and in some embodiments, up to 96 wt. %, or up to 95 wt. %) of a second solvent, C. 0-40 wt. % viscosity modifier, and D. 0-50 wt. % (or 1-20 wt. %) other additives (i.e., other than the components A, B, and C).

The second polymer matrix component A can be substantially free of water (includes less than 5 wt. % water, or less than 1 wt. % water). In some embodiments, no water is used in forming the second composition. Additionally, the components used in forming the second composition may be dry, and may be anhydrous, where possible. The second polymer matrix component is preferably not soluble in the first solvent.

The second polymer matrix component A can be a copolymer including polystyrene end blocks and polyalkylene and/or polydiene mid-block(s), e.g., including one or more of polyisoprene, polybutadiene, poly(ethylene-butylene), and poly(ethylene-propylene).

Copolymers including polystyrene end blocks and midblocks of polyisoprene or polybutadiene are commercially available under the trade name Kraton® D. Copolymers including polystyrene end blocks and poly(ethylene-butylene) or poly(ethylene-propylene) mid-blocks are commercially available under the trade name Kraton® G.

Exemplary polystyrene-based copolymers include those available under the tradenames Kraton® FG1901 and Kraton® G1652. The Kraton® FG1901 material is a clear, linear triblock copolymer based on styrene and ethylene/butadiene with a styrene content of about 30%. The Kraton® G1652 material is a clear or translucent linear triblock copolymer based on styrene and ethylene/butylene (SEBS) with a styrene/rubber ratio of 30/70.

The second solvent B is a safe, non-toxic solvent. The second solvent is incompatible with the first solvent. The second polymer matrix component is soluble in the second solvent but the first polymer matrix component is not soluble in the second solvent. In some embodiments, the second solvent B is heptane. Advantageously, heptane has been found to be incompatible with the first layer materials.

The viscosity modified C can be the same or different as the viscosity modifier listed above in the first composition.

The additives D can include any of the additives listed above as possible components in the first composition. In addition to these additives, oral care agents may also be included in the second layer. Other possible additives include thermochromics and color-changing additives. These types of additives may enable a user to visually determine when a treatment is complete.

In exemplary embodiments, the barrier layer contains a mixture of:

A. at least 5 wt. % of a styrene-ethylene/butylene block copolymer, such as Kraton® G1652, or at least 10 wt. %, or at least 15 wt. %, or at least 18 wt. %, and in some embodiments, up to 30 wt. %, or up to 25 wt. %, or up to 22 wt. %.

B. A non-polar solvent, from 6-26 wt. % butyl acetate (e.g., from 11-21 wt. %, or 14-18 wt. %), and from 44-84 wt. % heptane (e.g., from 54-74 wt. %, or 60-70 wt. %)

The mixture of A and B may be combined with other components C, in the amounts noted above.

In other exemplary embodiments, the barrier layer contains a mixture including:

A. at least 3 wt. % of a styrene-ethylene/butadiene block copolymer such as Kraton® FG1901, e.g., at least 4 wt. %, or at least 6 wt. %, or at least 7 wt. %, and in some embodiments, up to 20 wt. %, or up to 12 wt. % or up to 9 wt. %); and B. a non-polar solvent, such as at least 80 wt. % or at least 85 wt. %, or at least 90 wt. % heptane and in some embodiments, up to 96 wt. %, or up to 95 wt. %.

The mixture of A and B may be combined with other components C, in the amounts noted above.

The following examples, which are not intended to limit the scope of the invention, demonstrate how the release rate can be tailored using different release rate modifiers and provide illustrative matrix compositions.

EXAMPLES

Example 1

Investigation of Influence of Polymer Blend on First Layer

Two screening varnishes were prepared. Screening Varnish 1 was based on Eudragit® RL PO. Screening Varnish 2 was based on Eudragit® L 100-55. Both screening varnishes included carbamide peroxide as the oral care agent and ethanol as the solvent. The compositions of these varnishes (% by weight) are provided in Table 1.

TABLE 1

Compositions of Screening Varnishes

| | Screening Varnish 1 | Screening Varnish 2 |
|---|---|---|
| Carbamide Peroxide (g) | 8.3 | 8.3 |
| Ethanol (g) | 53.6 | 53.6 |
| Eudragit ® RL PO | 38.1 | — |
| Eudragit ® L 100-55 | — | 38.1 |

Sample varnishes were obtained by forming mixtures of the two screening varnishes in the proportions described in Table 2.

TABLE 2

Compositions of Sample Varnishes

| | Sample 1 | Sample 2 | Sample 3 | Sample 4 | Sample 5 | Sample 6 |
|---|---|---|---|---|---|---|
| Screening Varnish 1 (g) | 25 | 20 | 15 | 10 | 5 | — |
| Screening Varnish 2 (g) | — | 5 | 10 | 15 | 20 | 25 |

Each sample varnish was spread over a defined area and at a controlled thickness (50 μm, achieved through use of a tape template) onto a clean microscope slide. Varnishes were assessed based on their color (pre-curing), smell, and cure time. The completion of the curing was determined as the point at which the surface of the varnish ceased to be tacky to the touch. Once cured, the microscope slides were immersed in water for 30 minutes. After immersion, the slides were removed and the color of the varnishes was again assessed. Next, the ease of removal of the sample varnishes was determined by brushing the films with a Sonicare™ toothbrush while measuring the time required to remove the film.

Initial screening of the varnishes made mixing different ratios of Eudragit® L100-55 and Eudragit® RL PO revealed that each polymer introduced different properties to the final varnish. These differences were most extreme for Samples 1 and 6 which contained 100 wt. % of the RL PO-based varnish and 100 wt. % of the L100-55 varnish, respectively. Sample 1 cured to form a colorless layer which remained colorless during the 30-minute immersion in water. This varnish was difficult to remove from the surface of the microscope slide with Sonicare™ tooth brushing (i.e., little was removed after 2 minutes of brushing). The varnish that was removed tended to be small fragments, indicating that this varnish was, over time, quite brittle.

In contrast, the varnish of Sample 5 slid easily of the microscope slide following the 30-minute immersion. This varnish was malleable and did not fragment, suggesting that it could be peeled from teeth instead of brushed off. The varnish of Sample 6 became cloudy and opaque upon immersion in water. No significant difference was detected in the cure times of the varnishes of Samples 1 and 6.

Inspection of the varnishes prior to application to the slides revealed that both the RL PO-based and L100-55-based varnishes were colorless. The L100-55-based varnish was notably more viscous than the RL PO-based varnish. The absence of quaternary ammonium groups in L100-55 resulted in the varnish made entirely using this polymer being essentially odorless in comparison to the strong amine-like smell of the RL PO-based varnish. An odorless or reduced-smelling polymer enables a wider choice of fragrances and fragrance concentrations than a stronger-smelling polymer.

As the two polymers were mixed in different proportions (Samples 2-5), the varnish properties transitioned in proportion to the polymeric composition of the varnishes. The transitions were gradual and linear with no sudden changes in varnish properties as a function of polymer composition. Varnishes with less than 40 wt. % of L100-55 based on the polymer content remained essentially colorless following 30 minutes water immersion. Varnishes became easier to remove (by peeling) when the percentage of L100-55 exceeded 60 wt. % based on the polymer content.

A summary of the properties of Samples 1-5 is provided in Table 3.

TABLE 3

Properties of Samples 1-6

| | Sample 1 | Sample 2 | Sample 3 | Sample 4 | Sample 5 | Sample 6 |
|---|---|---|---|---|---|---|
| Smell | Amine smell (from polymer) | Faint polymer smell | Very faint polymer smell | Slight background smell - mostly ethanol | Odorless (only solvent smell) | Odorless (only solvent smell) |
| Cure time (applied at 50 μm) | About 50 seconds | About 50 seconds | About 50 seconds | About 50 seconds | About 50 seconds | About 50 seconds |
| Hardness/ Removability (after immersion) | Hard/brittle. Not readily removable. | Hard/brittle. Not readily removable. | Hard, some removal detected after 1 minute Sonicare™ brushing | Soft, peeled from microscope slide after 1 minute brushing. Film malleable. | Soft, peeled from microscope slide after 1 minute brushing. Film malleable. | Very soft. Slides off microscope slide. |

Example 2

Investigation of Qualitative Influence of Composition on Viscosity

Three different first layer varnish compositions were prepared. The ratio of RL PO:L100-55 was 70:30 for each composition. Hydrogen peroxide in solution (41.84 wt. % in water) was used as the oral care agent and ethanol as the solvent. The compositions of each of the varnishes are provided in Table 4.

TABLE 4

Compositions and Viscosity for Samples 7-9

|  | Sample 7 | Sample 8 | Sample 9 |
|---|---|---|---|
| Ethanol (g/100 g) | 43.65 | 50 | 55 |
| RL PO (g/100 g) | 29.4 | 24.95 | 21.45 |
| L100-55 (g/100 g) | 12.6 | 10.70 | 9.2 |
| Hydrogen peroxide solution (g/100 g) | 14.35 | 14.35 | 14.35 |
| Actual hydrogen peroxide concentration in sample (g/100 g) | 6.00 | 6.00 | 6.00 |
| Viscosity | High | Intermediate | Low |

Viscosity decreased as the ratio of ethanol:polymer increased.

Example 3

Investigation of Quantitative Influence of Composition on Viscosity

Seven different first layer varnish compositions were produced for quantitative viscosity analysis. The ratio of L100-55:RL PO was varied and viscosity was plotted as a function of shear rate and percentage of L100-55. Hydrogen peroxide solution (41.84 wt. % stock) was used. The compositions of Samples 10-16 are provided in Table 5.

TABLE 5

Compositions of Samples 10-16

|  | Sample 10 | Sample 11 | Sample 12 | Sample 13 | Sample 14 | Sample 15 | Sample 16 |
|---|---|---|---|---|---|---|---|
| Hydrogen peroxide solution (g/100 g) | 14.34 | 14.34 | 14.34 | 14.34 | 14.34 | 14.34 | 14.34 |
| Ethanol (g/100 g) | 55 | 55 | 55 | 55 | 55 | 55 | 55 |
| L100-55 (g/100 g) | 27.59 | 23.00 | 18.40 | 13.80 | 9.20 | 4.60 | 0 |
| L100-55 (as a wt. % of total polymer composition) | 90 | 75 | 60 | 45 | 30 | 15 | 0 |
| RL PO (g/100 g) | 3.07 | 7.67 | 12.26 | 16.86 | 21.46 | 26.06 | 30.66 |
| RL PO (as a wt. % of total polymer composition) | 10 | 25 | 40 | 55 | 70 | 85 | 100 |

Solvent (i.e., ethanol) concentration was 55 wt. % for Samples 10-16. At low L100-55 concentrations (e.g., 0%, 15%, and 30 wt. %), varnish viscosity is low (maximum 0.8 Pa·s) and independent of increasing shear rate (Newtonian behavior). As the L100-55 content, and with it viscosity) increases (greater than 45 wt. % L100-55), the measured viscosity decreases as a function of increasing shear rate (shear thinning) This property may be advantageous for stirring and/or applying the composition. Viscosity as a function of shear rate and L100-55 percentage is plotted in FIG. 4.

Figure 4:
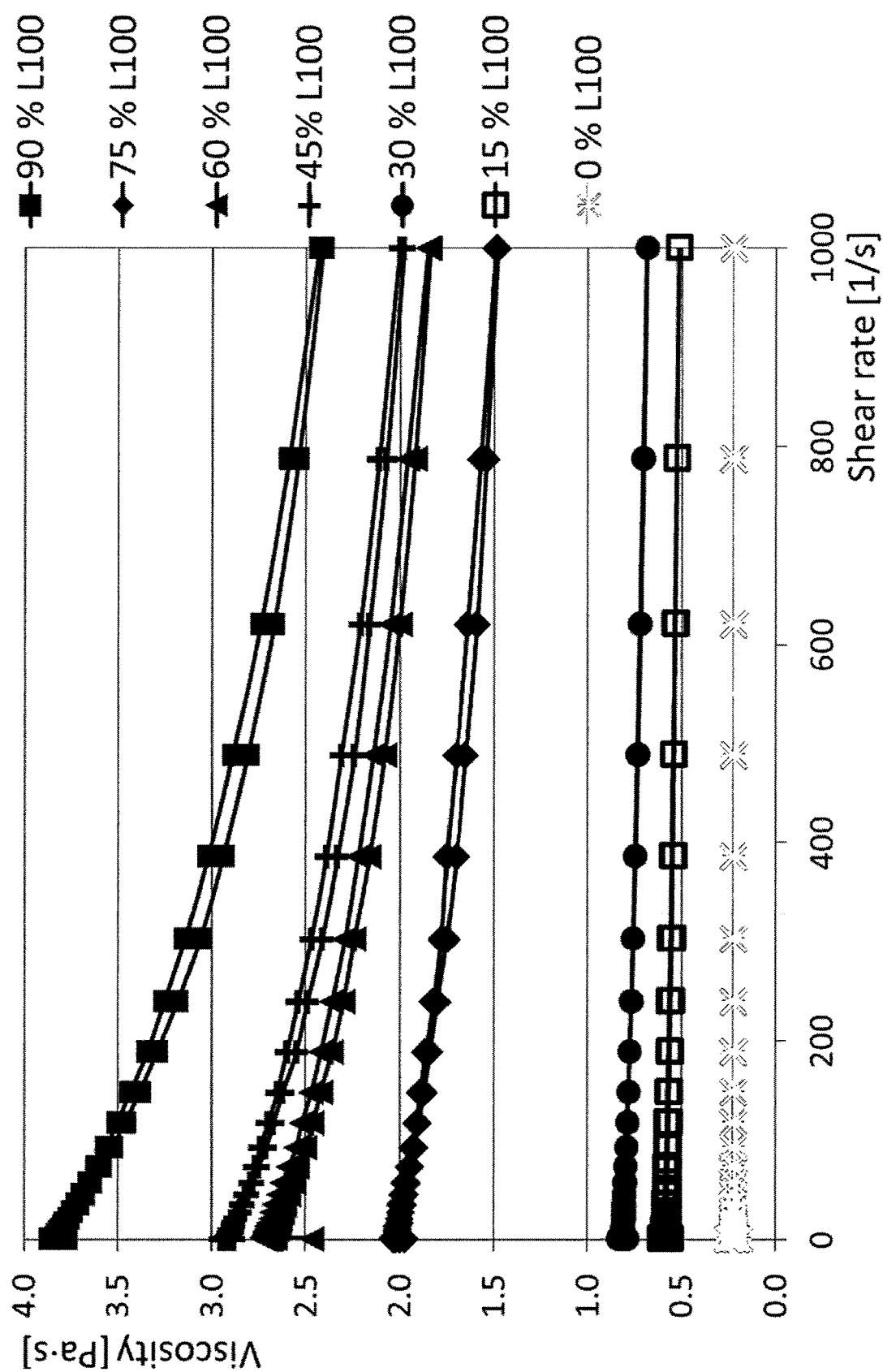
FIG. 4 is a graph illustrating the effect of matrix polymer composition on viscosity.

FIG. 4 illustrates that viscosity generally increases with increasing L100-55 content. However, this trend is not linear and some deviation is observed. It may be desirable to avoid conditions and compositions close to where the viscosity properties change. Accordingly, compositions that do not contain between 30% and 45% L100-55 wt % are particularly suitable.

Beyond this step, the trend in varnish viscosity is less clear. Viscosity appears to decrease beyond 45% L100-55 (dropping from 2 and 3 Pa·s for high and low shear measurements, respectively, to 1.5 and 2 Pa·s) before increasing again for the 90% L100-55 varnish (2.4 and 3.8, respectively). Without wishing to be bound by theory, it is believed that the apparent decrease in varnish viscosity beyond 45% L100-55 when higher proportions of L100-55 are used results from incompatibility (or immiscibility) of the polymer components, particularly at higher L100-55 concentrations.

Example 4

Curing Rate Investigation

Curing times for nine identical compositions were determined using distinct combinations of deposited layer thickness (i.e., thickness prior to curing) and air flow rate. The composition was the same as that of Sample 8 in Table 4. The three different thicknesses tested were 30 μm, 50 μm, and 110 μm. The three air flow rates tested were 0 L/min (i.e., no air flow), 8.75 L/min, and 135 L/min. The results for the curing/drying times of Samples 17-25 are provided in Table 6.

TABLE 6

Drying/curing times for Samples 17-25

| | | Applied Varnish Thickness | | |
|---|---|---|---|---|
| | | 30 μm | 50 μm | 110 μm |
| Air Flow Rate | None | Sample 17: 55 seconds | Sample 18: 130 seconds | Sample 19: 340 seconds |
| | 8.75 L/min | Sample 20: 13 seconds | Sample 21: 24 seconds | Sample 22: 125 seconds |
| | 135 L/min | Sample 23: 7 seconds | Sample 24: 21 seconds | Sample 25: 41 seconds |

Curing time was measured as the time required for the deposited varnish to cease being tacky. The relationship between thickness and curing time is non-linear. For example, doubling applied thickness more than doubles cure time. The non-linear relationship suggests that curing rate is determined by more than simply solvent evaporation from the film. One potential factor is chemical change to the film. It is believed that curing in these thicker films occurs fastest at the surface, slowing solvent evaporation from lower layers.

Air flow was directed at the deposited varnish layer via a fan positioned about 2.5 cm above the film. Introduction of an 8.75 L/min air flow (delivered by a 3V fan) reduced the curing time by 60-80% when compared to experiments in the absence of introduced air flow. Increasing the air flow rate to 135 L/min (delivered via a larger 12V fan) further reduced the curing time by 85-90% when compared to experiments in the absence of air flow. Thus, significant increase in the power and size requirements of the fan only resulted in a modest (10-20%) curing time reduction in comparison to the smaller, low-powered fan.

Example 5

Petroleum Jelly Second (Barrier) Layer Tests

Experiments were conducted to determine the effectiveness of petroleum jelly barrier layers. In comparative Sample 26, a single layer whitening varnish (70:39 RL PO:L100-55) was immersed in a phosphate buffered saline (PBS) solution for 30 minutes. The control sample released 100% of its hydrogen peroxide within 5 minutes of immersion. After removal from the PBS solution, the varnish had become slightly milky in appearance (from colorless when dry) but remained transparent.

Figure 5:
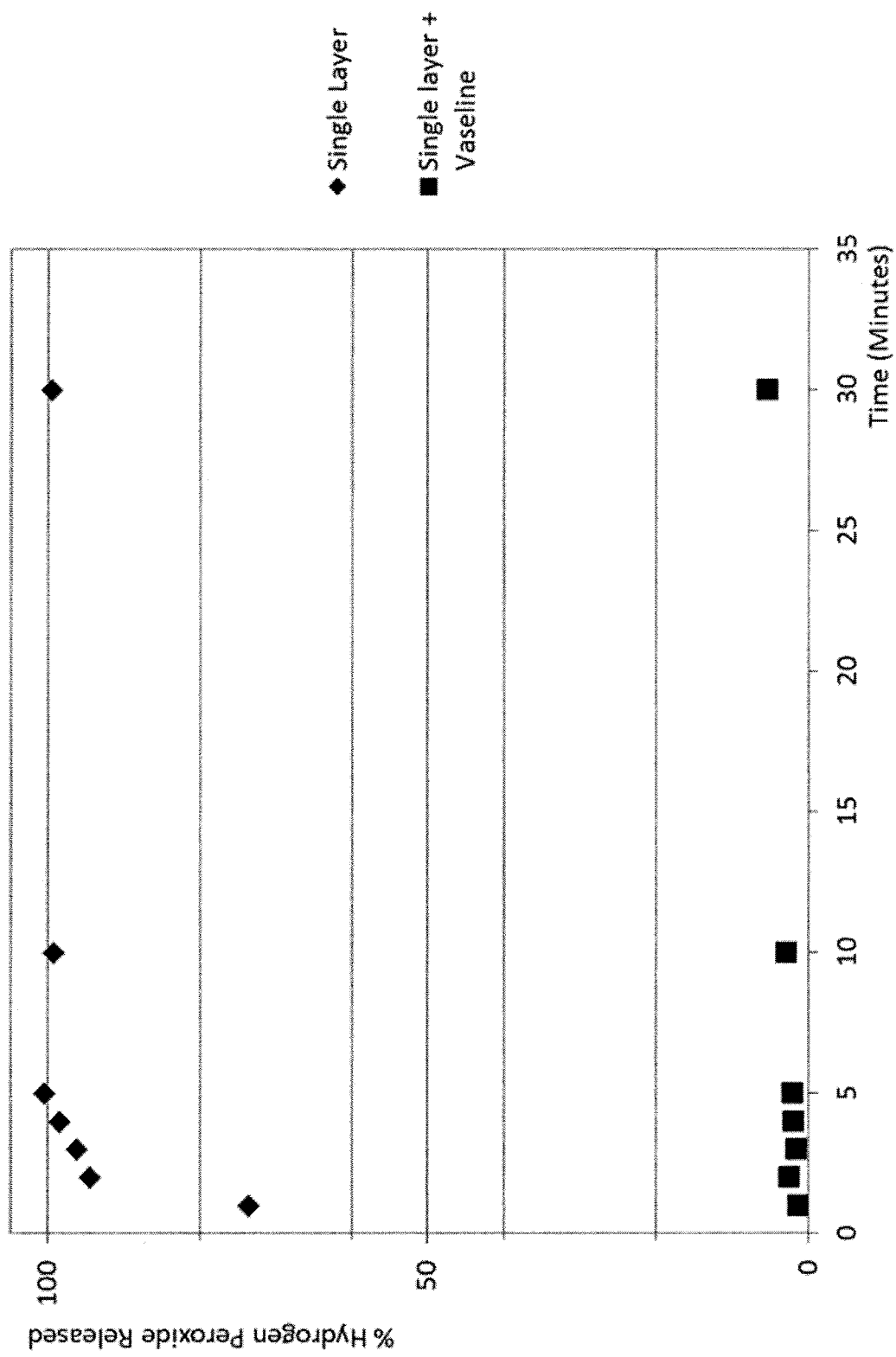
FIG. 5 is a graph illustrating the difference in hydrogen peroxide release in an immersion test between a dual layer system of the present disclosure and a single layer system.

In Sample 27, the general procedure of comparative Sample 26 was followed but a layer of petroleum jelly was applied to the whitening varnish layer prior to immersion in PBS. The petroleum jelly barrier layer significantly reduced the rate of peroxide release. After the 30-minute immersion, about 5% of the peroxide had been released. Inspection of the whitening varnish layer, underneath the petroleum jelly barrier layer, revealed that the whitening varnish layer had remained colorless, suggesting that water uptake may have played a role in the discoloration in comparative Sample 26. FIG. 5 illustrates the percentage of hydrogen peroxide released over time for comparative Sample 26 (denoted "Single Layer") and Sample 27 (denoted "Single layer+Vaseline").

Figure 6:
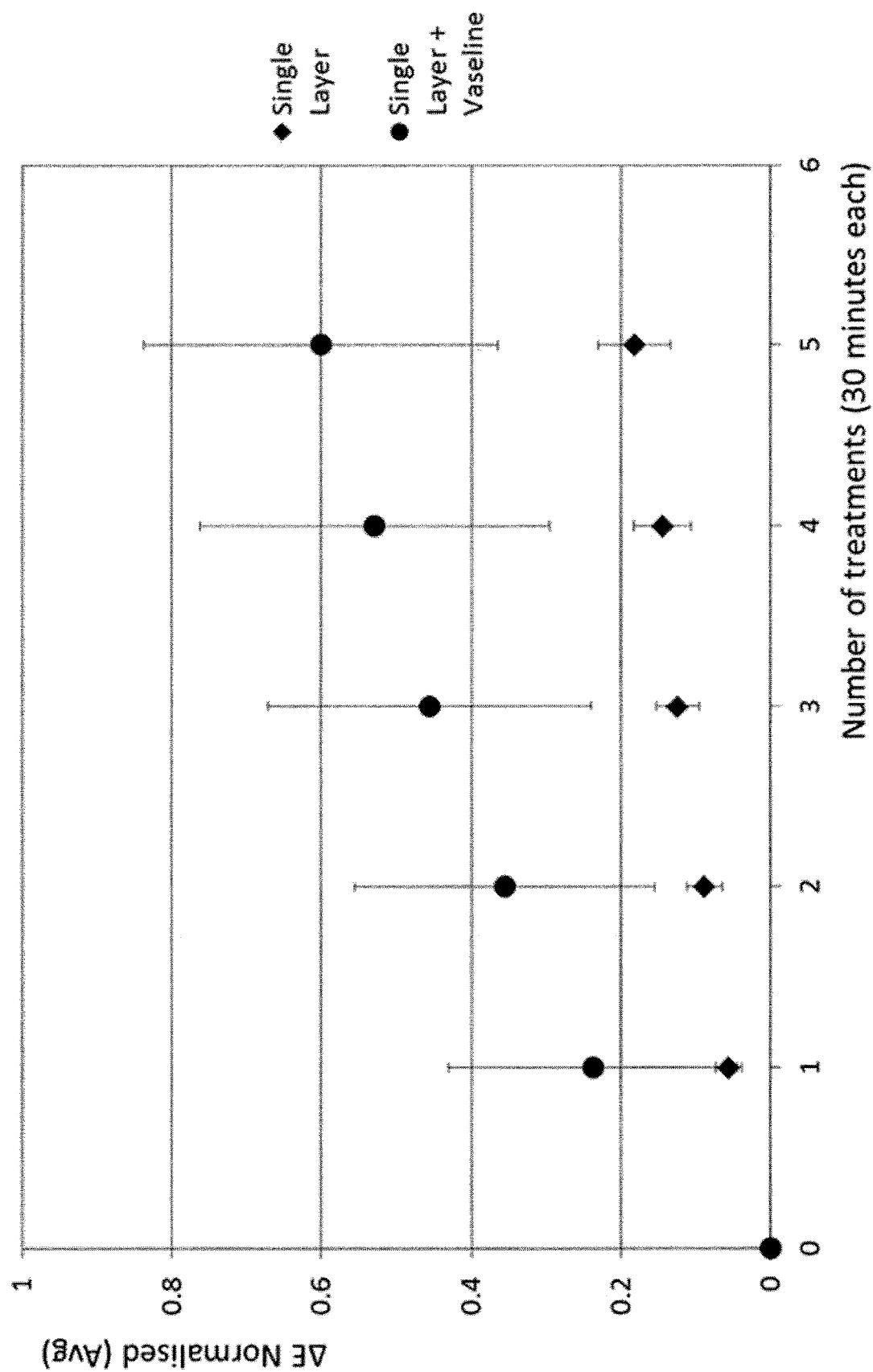
FIG. 6 is a chart illustrating the ΔE data following treatment using a dual layer system of the present disclosure compared to a single layer system.
Figure 7:
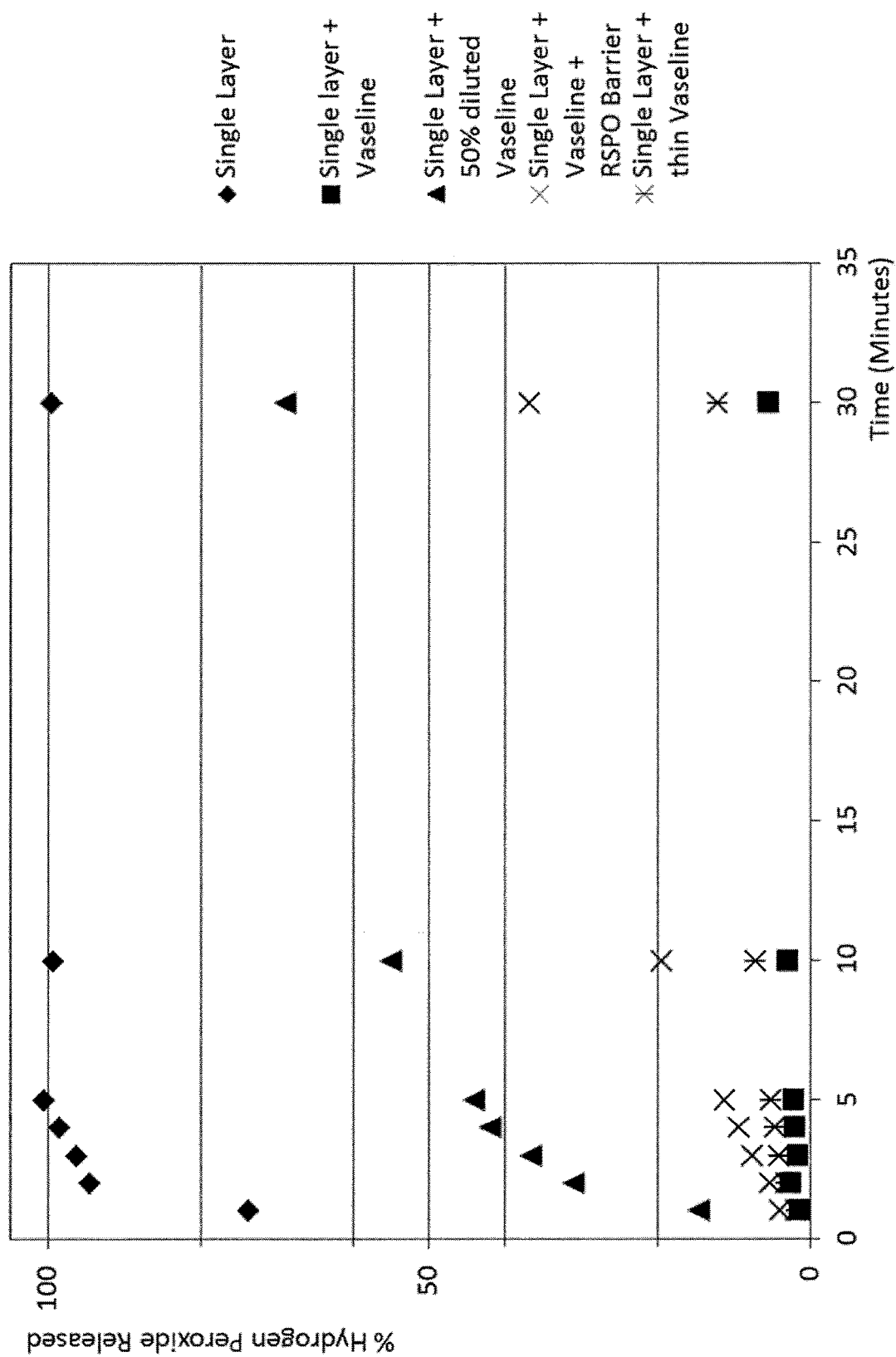
FIG. 7 is a graph illustrating hydrogen peroxide release profiles for various barrier layers of the present disclosure.
Figure 8:
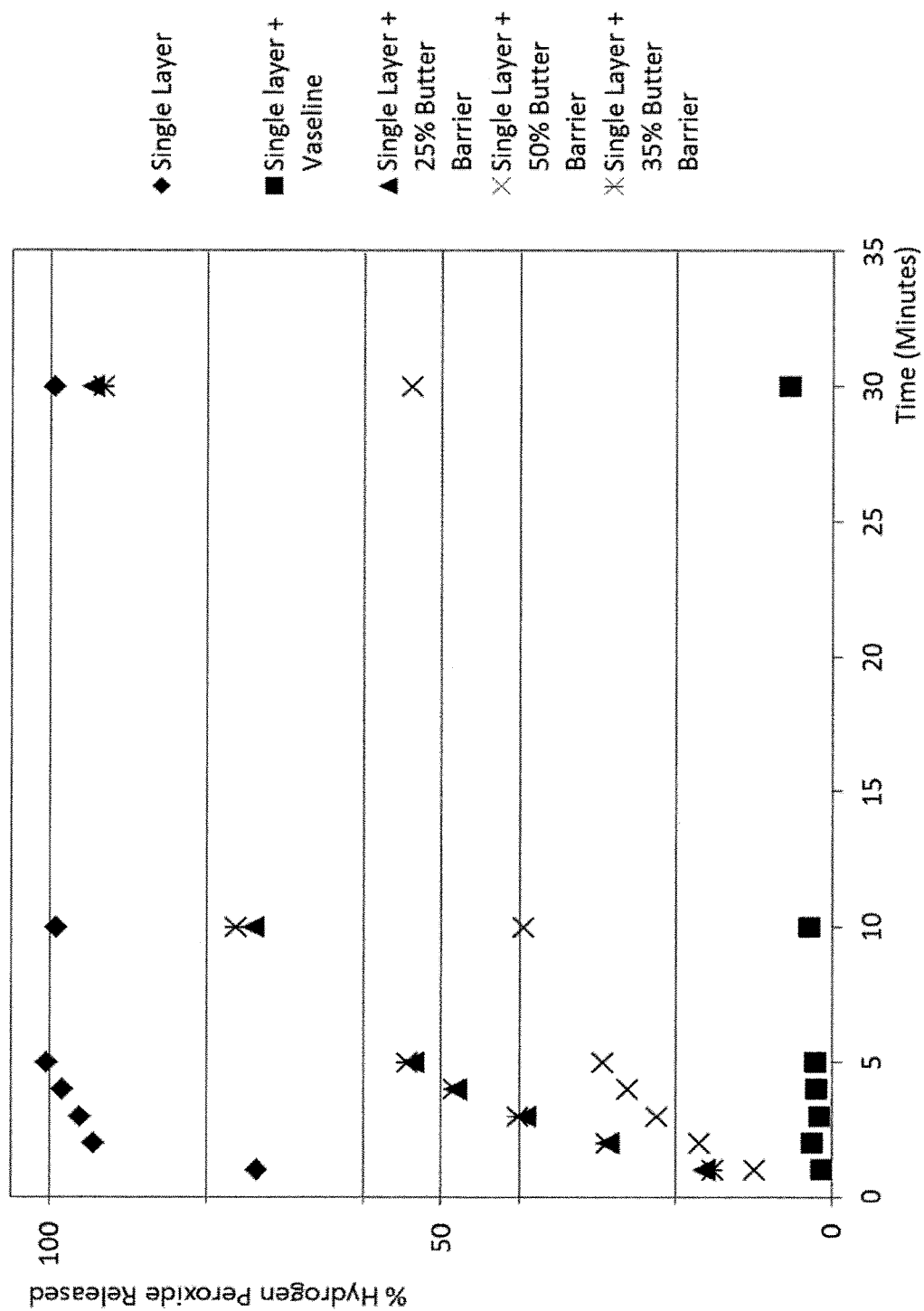
FIG. 8 is a graph illustrating hydrogen peroxide release profiles for various barrier layers of the present disclosure.

Bovine teeth testing was conducted to determine the efficacy of treatments with the single layer system of comparative Sample 26 and the dual layer system of Sample 27. The experiments were conducted with the bovine teeth fully immersed in water. On a normalized axis (normalized to the extent of staining each tooth took up), the petroleum jelly-covered teeth showed an improvement of the times in whitening efficacy when compared to the teeth that were not covered with petroleum jelly (about 0.6 versus 0.2, respectively) following 10×30-minute treatments. These results corresponded to average ΔE values of 7.0 and 2.5, respectively. The results are illustrated in FIG. 6. The uncertainty in the data for the petroleum jelly-covered teeth (as indicated by the error bars) is greater than that observed for the teeth that were treated with the single layer system. Without wishing to be bound by theory, it is believed that this difference reflects differences in the structures of individual teeth and the extent to which they had taken up the stain. The variance may be more significant in the petroleum jelly-covered teeth because the peroxide is resident on the teeth for a longer time period and so better resolves the influence of tooth structure on staining/whitening than the shorter-residence time, superficial whitening of the teeth when the single layer system was used.

Several other release tests were conducted to compare the effectiveness of the petroleum jelly to other barrier coatings. These results are illustrated in FIGS. 7-15.

Many potential barrier layers were screened using the same peroxide release assay used for the Vaseline experiments described above. Results were compared to those obtained from the Vaseline-covered and unprotected varnish since the correlation between these results and whitening efficacy was already established (above).

Example 6

Non-Cured Barrier Layers

To make the second layer more palatable and comfortable in feel, experiments were conducted on various potential second layers. One experiment involved diluting Vaseline (petroleum jelly) with 50% mineral oil. This reduced the viscosity of the Vaseline making it sufficiently liquid to be brush-applied to the teeth. However, diluting the Vaseline and brush-applying it to the whitening layer in this way resulted in a much thinner layer of Vaseline being applied and this was consequently a less effective barrier to hydrogen peroxide release (about 70% release following 30-minutes immersion in water, compared to about 5% release for finger-applied undiluted Vaseline).

To limit the extent to which the tongue can interact with the Vaseline barrier layer, the utility of a third, cured, layer 26 was investigated. This varnish layer (Eudragit RSPO in ethanol—no hydrogen peroxide) was applied on top of a thin (50 µm) Vaseline layer applied on top of a whitening layer. Eudragit RSPO was easily applied on top of the Vaseline layer and cured there to form a robust layer, likely to withstand 30-minutes wear time in the mouth. Peroxide release profiles from varnish films coated in this way indicate a decrease in the efficacy of the layer in preventing peroxide release relative to a thin Vaseline layer (50 µm—original varnish experiments were conducted with a Vaseline layer about 500 µm thick) used without varnish protection (peroxide release after 30-minutes immersion 35% for layers coated with Vaseline and varnish compared to 12% for varnish layers coated with a thin Vaseline-layer only). The decrease in efficacy of the Vaseline-layer when coated with varnish perhaps suggests a disturbance of this layer upon brush application, which could possibly have been reduced with a thicker first Vaseline layer. These results are presented in FIG. 7.

Varnishes made with a mixture of 1-oleoyl-rac-glycerol (ERO) (monoolein) and Eudragit RSPO in ethanol offered the combination of a non-polar/oily component (like Vaseline) delivered in a solvent-cured varnish. Experiments focused on adjusting the polymer:1-oleoyl-rac-glycerol ratio to improve the performance of the varnish in blocking peroxide release whilst maintaining a curable varnish layer. The varnish was formulated with 51% ethanol and 49% combined polymer plus 1-oleoyl-rac-glycerol. Below, the percentages used refers to the percentage of this latter component.

Peroxide release profiles from varnishes coated with 25% and 35% ERO/RSPO varnish were indistinguishable. After 30-minutes water immersion these varnishes had released >90% of their hydrogen peroxide (FIG. 8), however peroxide release over this period was significantly slower than for the unprotected varnish (about 50% following 5 minutes immersion compared to 100% for the unprotected varnish). This suggests that whitening efficiency may still be benefitted by such a layer.

Increasing the ERO:RSPO ratio of the varnish to 50:50 significantly reduced the extent to which the varnish cured.

Example 7

Eudragit Polymers in Ethanol and Ethyl Acetate

Figure 9:
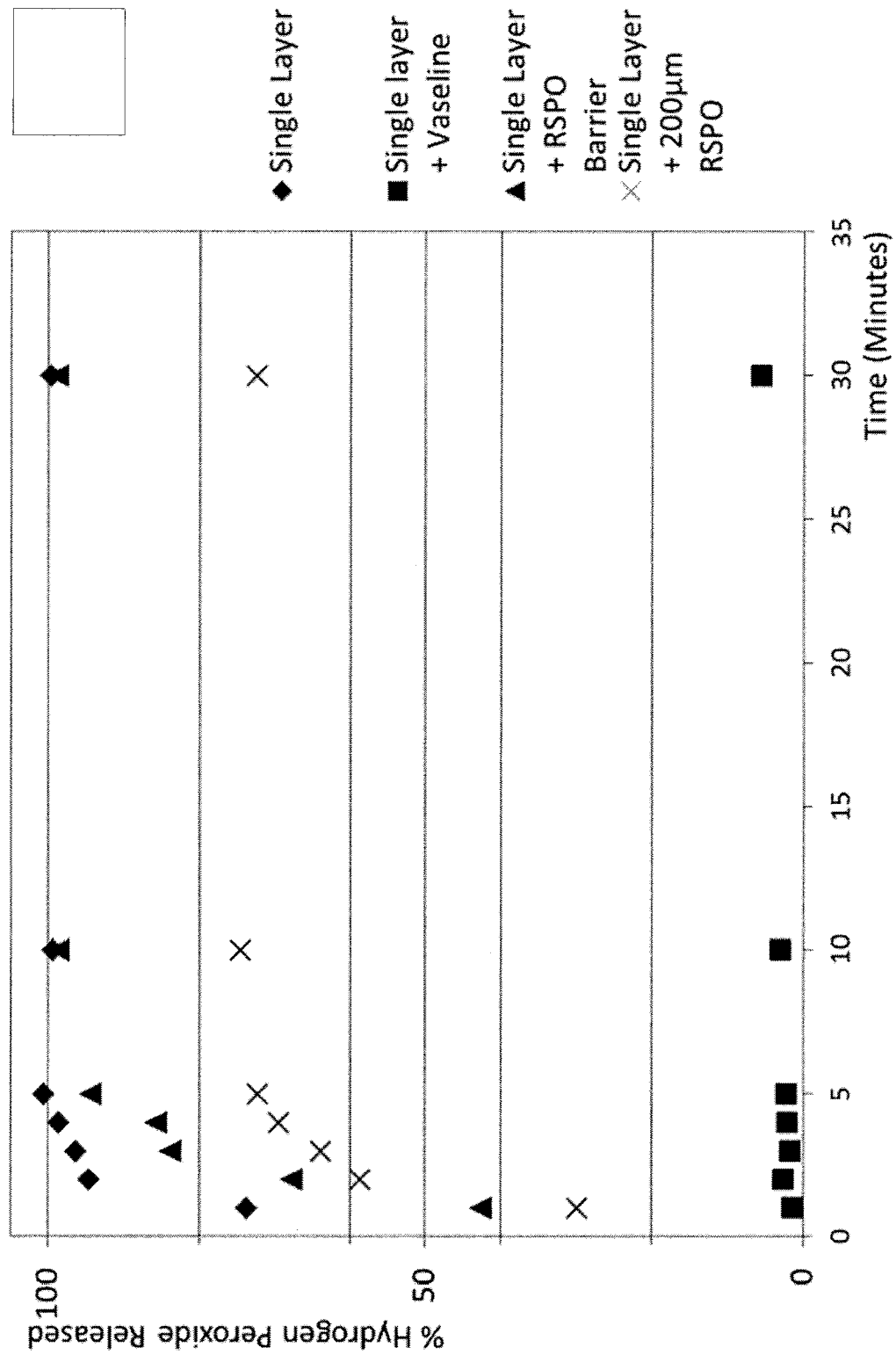
FIG. 9 is a graph illustrating hydrogen peroxide release profiles for various barrier layers of the present disclosure.
Figure 10:
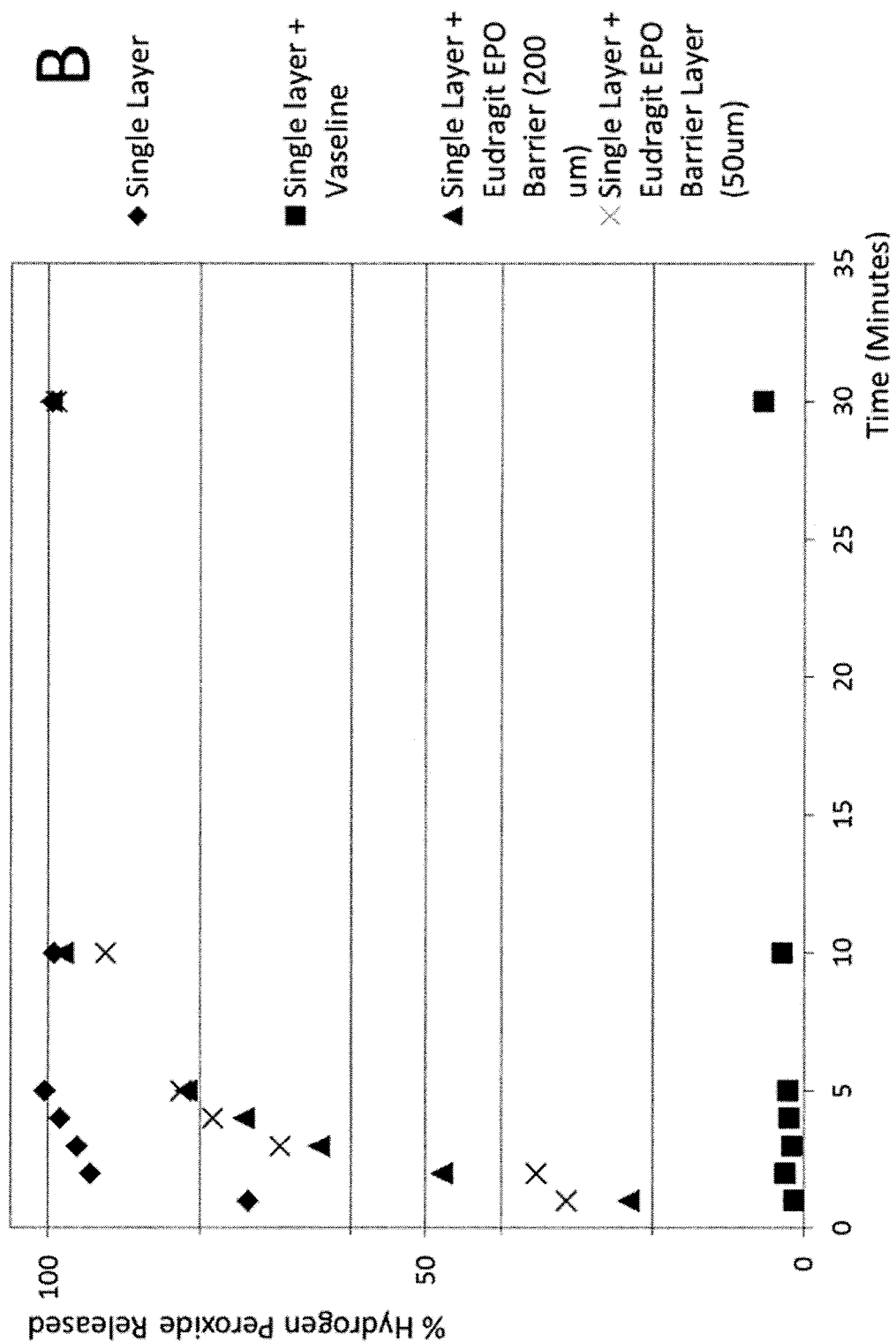
FIG. 10 is a graph illustrating hydrogen peroxide release profiles for various barrier layers of the present disclosure.
Figure 11:
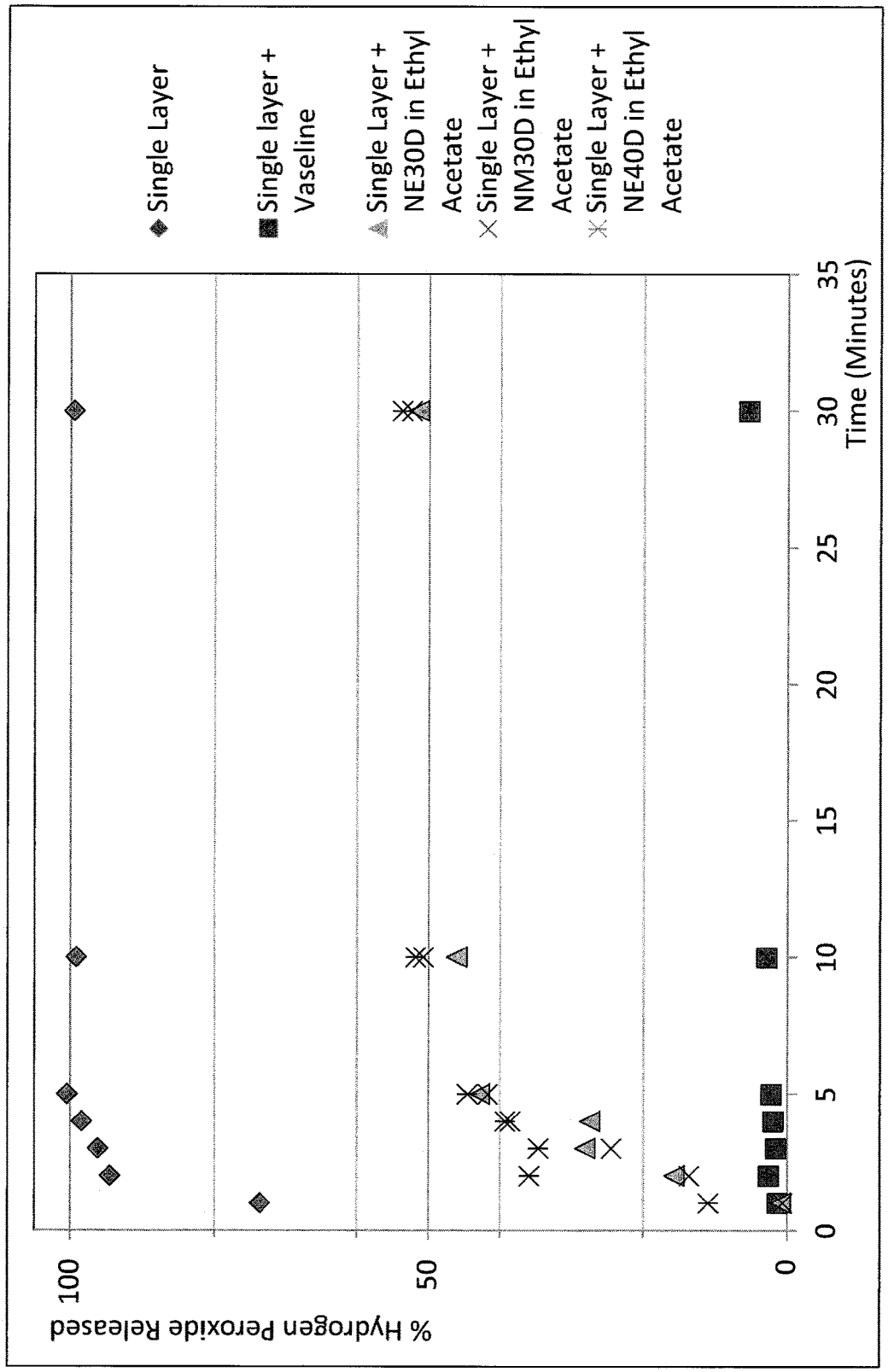
FIG. 11 is a graph illustrating hydrogen peroxide release profiles for various barrier layers of the present disclosure.
Figure 12:
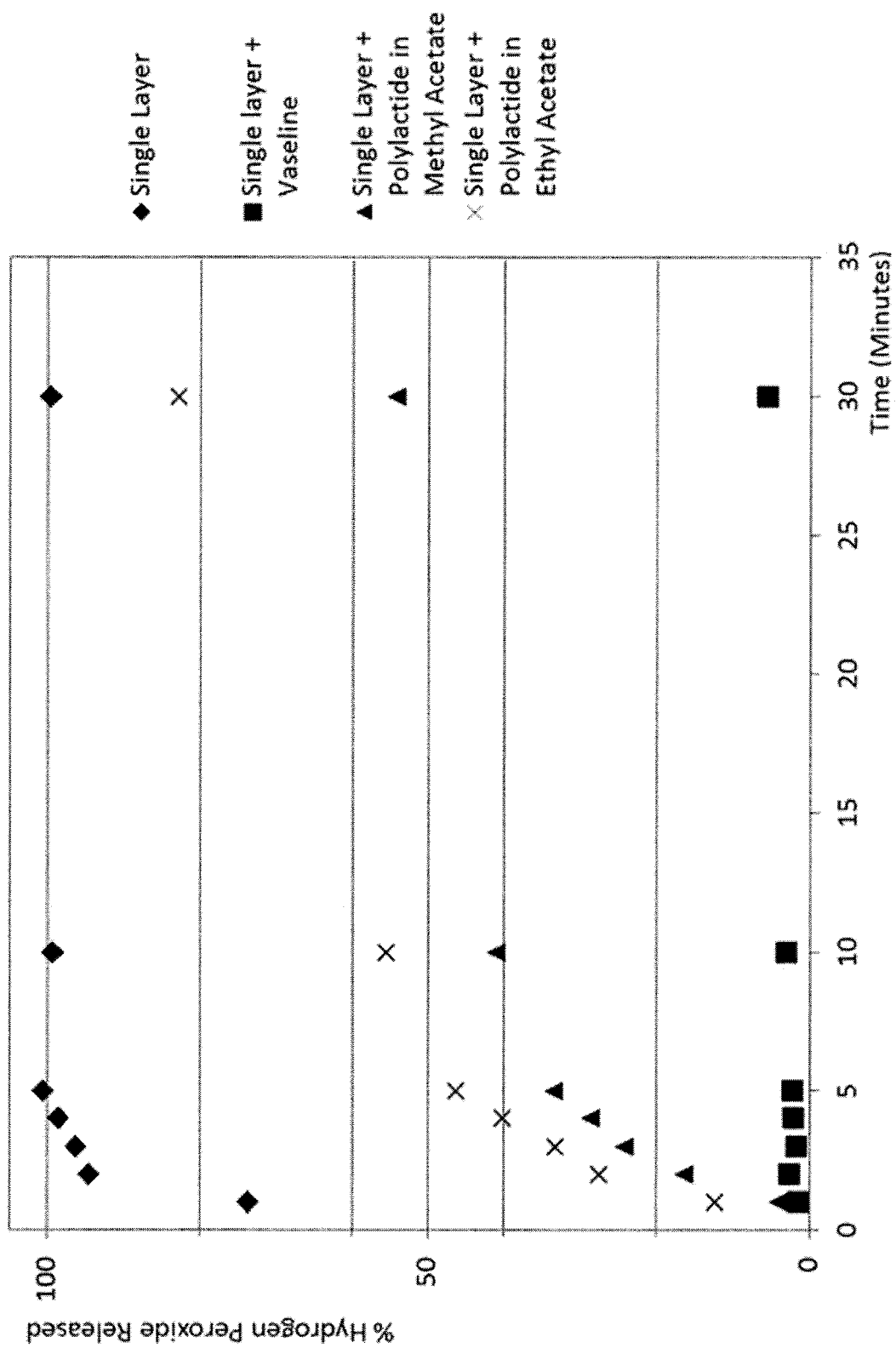
FIG. 12 is a graph illustrating hydrogen peroxide release profiles for various barrier layers of the present disclosure.
Figure 13:
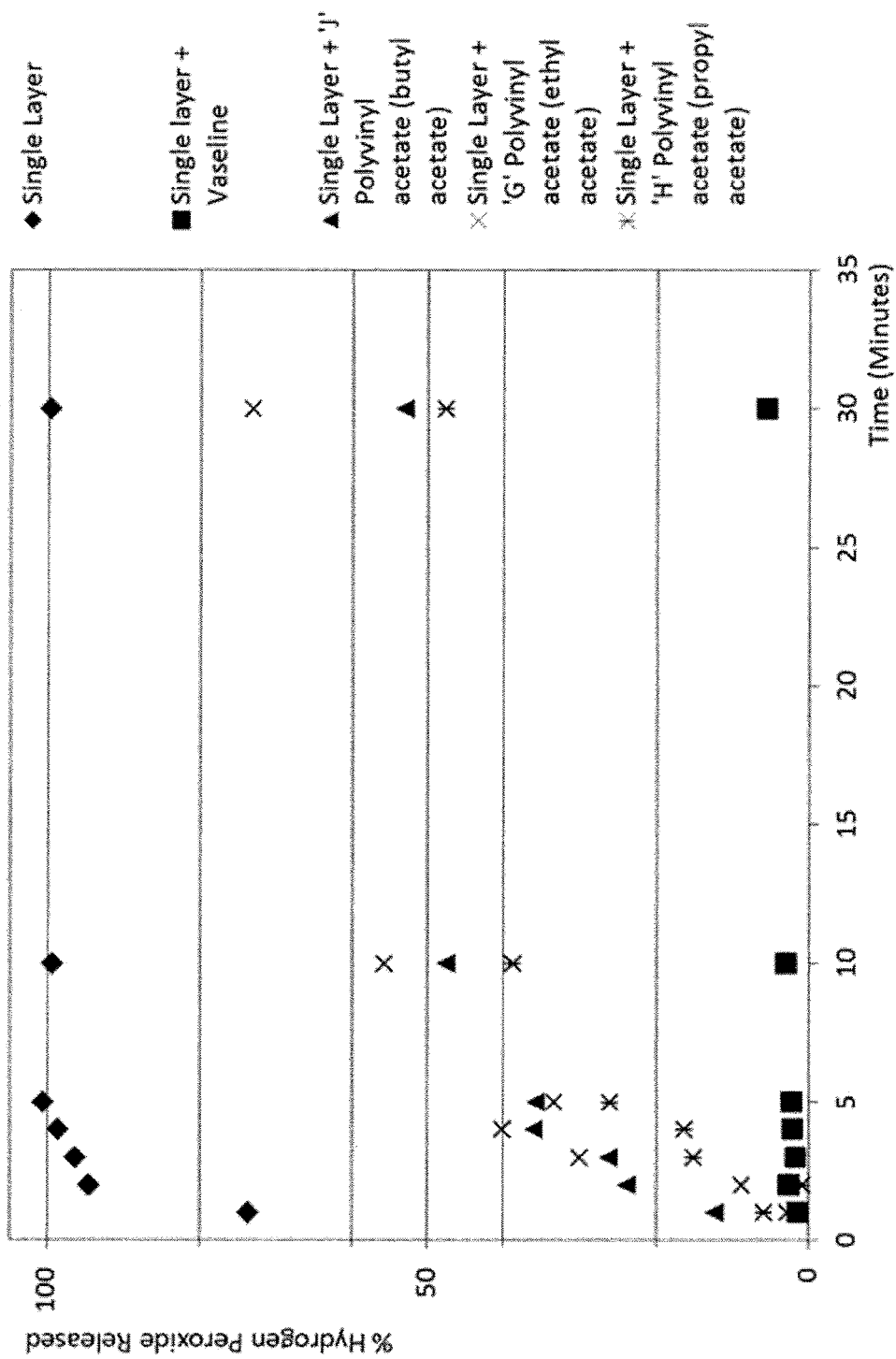
FIG. 13 is a graph illustrating hydrogen peroxide release profiles for various barrier layers of the present disclosure.
Figure 14:
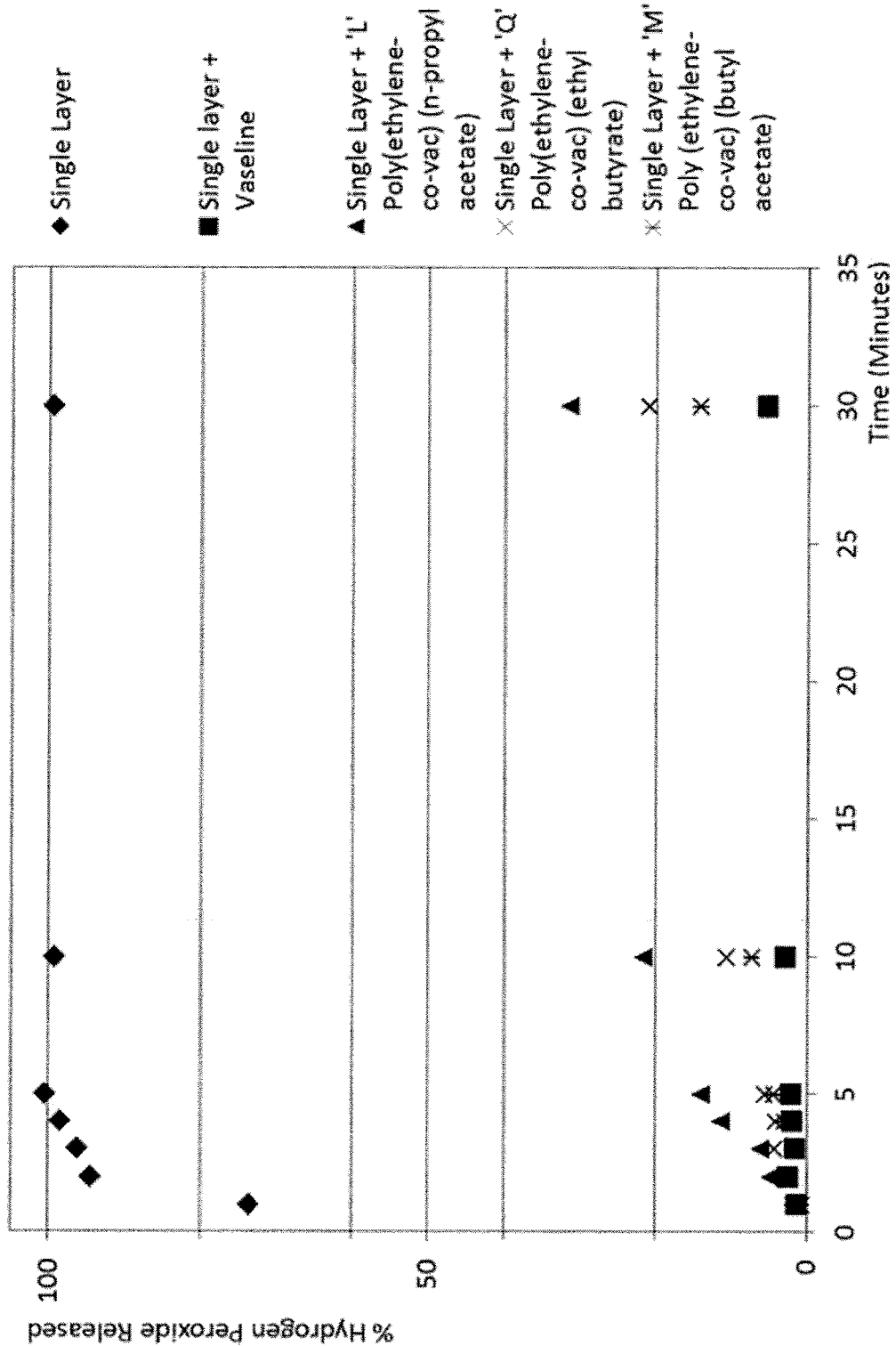
FIG. 14 is a graph illustrating hydrogen peroxide release profiles for various barrier layers of the present disclosure.
Figure 15:
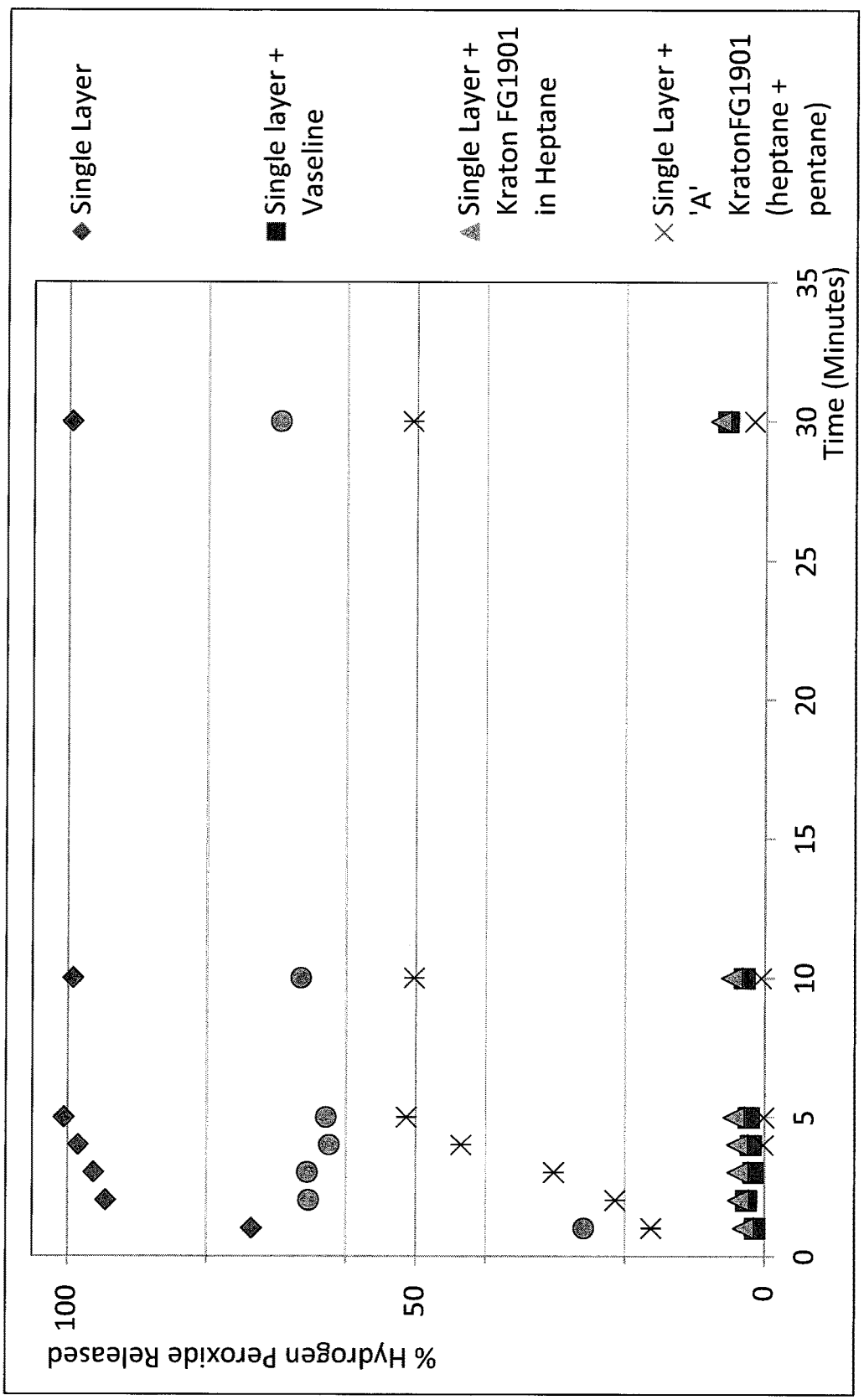
FIG. 15 is a graph illustrating hydrogen peroxide release profiles for various barrier layers of the present disclosure.

A layer of Eudragit RSPO and EPO was found to slow the hydrogen peroxide release in the initial 10 minutes (95% and 82% release after 5-minutes for RSPO and EPO respectively vs. 100% at the same time point for the unprotected varnish) following 30 minutes immersion varnishes coated with both polymers had released 100% of their hydrogen peroxide (FIGS. 9 and 10).

Increasing the thickness of these protective polymer layers had different effects on the hydrogen peroxide release profile. Increasing the thickness of Eudragit EPO applied to the whitening varnish from 50 to 200 μm had no discernible effect on peroxide release from the varnish (FIG. 10). By contrast, a similar increase in thickness of the Eudragit RSPO layer reduced the peroxide release following 30-minutes immersion to about 70% (FIG. 9). The lower permeability of Eudragit RSPO at near neutral pH when compared to Eudragit EPO may explain the difference.

Experiments were also conducted using the Eudragit polymers NE 30D, NE 40D and NM 30D mixed in ethyl acetate as barrier layers. These polymers are sold as aqueous suspensions and therefore had to be dried and re-suspended in solvent before use. Varnishes made using these polymers cured to form clear highly flexible layers (a consequence of the low Tg of these polymers). The results are presented in FIG. 11.

The hydrogen peroxide release profiles of varnishes coated with these three polymers were comparable to each other and a significant improvement on the ethanol-based formulations (RSPO and EPO) described above (about 50% release following a 30 minute immersion). This may be due in part to the solvent used.

Example 8

Influence of Solvent on Barrier Layer Peroxide Release Rates

Analysis of the peroxide release profiles observed from polylactide-, polyvinyl acetate- and poly(ethylene-co-vac)- as barrier layers (FIGS. 12-14) suggests a strong influence on the solvent used. Peroxide release is observed between varnishes made with different solvents following a 30-minute immersion in water. The release from polyvinyl acetate-coated varnishes was 73% with ethyl acetate as solvent and about 50% with butyl- or propyl acetate as solvent. Comparing all three graphs (FIGS. 12-14) it can be seen that peroxide release from varnishes decreases as the solvent in which they are dissolved increases in the hydrocarbon chain length: methyl, ethyl, propyl and butyl acetate. For poly(ethylene-co-vac), peroxide release after 30 minute immersion in water was 31, 21 and 14% for ethyl(butyrate), propyl and butyl acetate respectively—FIG. 14).

All three of these polymers continue to offer protection against peroxide release beyond 30-minutes immersion in water. When tested using the same solvent, ethyl acetate, following 30-minutes immersion, varnishes coated with polylactide released 83% total peroxide, polyvinyl acetate released 73%. Likewise, varnishes coated with a polyvinyl acetate-based barrier layer in butyl acetate release 52% peroxide in 30-minutes compared to 14% for poly(ethylene-co-vac) in the same solvent.

Vaseline layer (poly(ethylene-co-vac)) in butyl acetate in comparison showed a 14% release in 30-minutes compared to about 5% for the Vaseline-coated varnish.

Varnishes protected with Kraton FG1901 dissolved in the esters, propyl acetate and butyl acetate, showed similar trends in hydrogen peroxide release profile to the polylactide and poly(ethylene-co-vac) varnishes described above. Hydrogen peroxide release was higher from the varnish coated with Kraton dissolved in propyl acetate when compared to the polymer dissolved in butyl acetate (70% vs. 50% respectively).

A significant improvement in the performance of the Kraton FG1901 polymer as a barrier layer was observed when dissolved in the non-ester solvents heptane and pentane. Peroxide release from the varnish coated in Kraton FG1901 dissolved in heptane was equivalent to that observed when Vaseline was used (6.5% release following 30 minutes immersion—compared to 50% when the polymer was dissolved in butyl acetate). Dissolving the polymer in a mixture of heptane and pentane (at 50:50) further improved the peroxide release performance during 30 minutes immersion (decreased to <2%-4% lower than achieved from Vaseline). These results are presented in FIG. 15.

Example 9

Second (Barrier) Layer Solvent Tests

The solvent in which the barrier layer polymer is dissolved has a significant effect on the efficacy of the barrier layer composition. Preferably, the barrier layer solvent does not interfere with the first layer (which contains the oral care agent).

To evaluate the effect of various solvents on the first layer, experiments were conducted by rinsing a whitening layer containing hydrogen peroxide with the various solvents. The amount of hydrogen peroxide retained in the layer was measured. A higher percentage of hydrogen peroxide retained in the whitening layer was indicative of less interference by the solvent. The results of the solvent tests are provided in Table 7.

TABLE 7

Hydrogen peroxide retention after rinsing with various solvents

| Solvent | Hydrogen Peroxide Retention |
| --- | --- |
| Water | 22% |
| Ethyl acetate | 14% |
| Propyl acetate | 14% |
| Butyl acetate | 28% |
| Heptane | 54% |
| Ethanol | 16% |
| Amyl Acetate | 21% |
| 2-Heptanone | 9.5% |
| Pentane | 88% |

Example 10

Release Characteristics of Second (Barrier) Layer Polymer Matrix Materials

Experiments were conducted by providing varnish compositions containing different polymers dissolved in the same solvent. The experiments showed that different polymers exhibited different release characteristics. Of the polymers investigated, Kraton® FG1901, Kraton® G1652, and ethylene vinyl acetate copolymer had the most effective release properties (e.g., low (<10%) peroxide release over the 30 minute duration of the experiment). Comparable release characteristics were observed when petroleum jelly was used. Petroleum jelly resulted in good whitening results.

Example 11

Effect of Applied Thickness on Whitening Result

Figure 16:
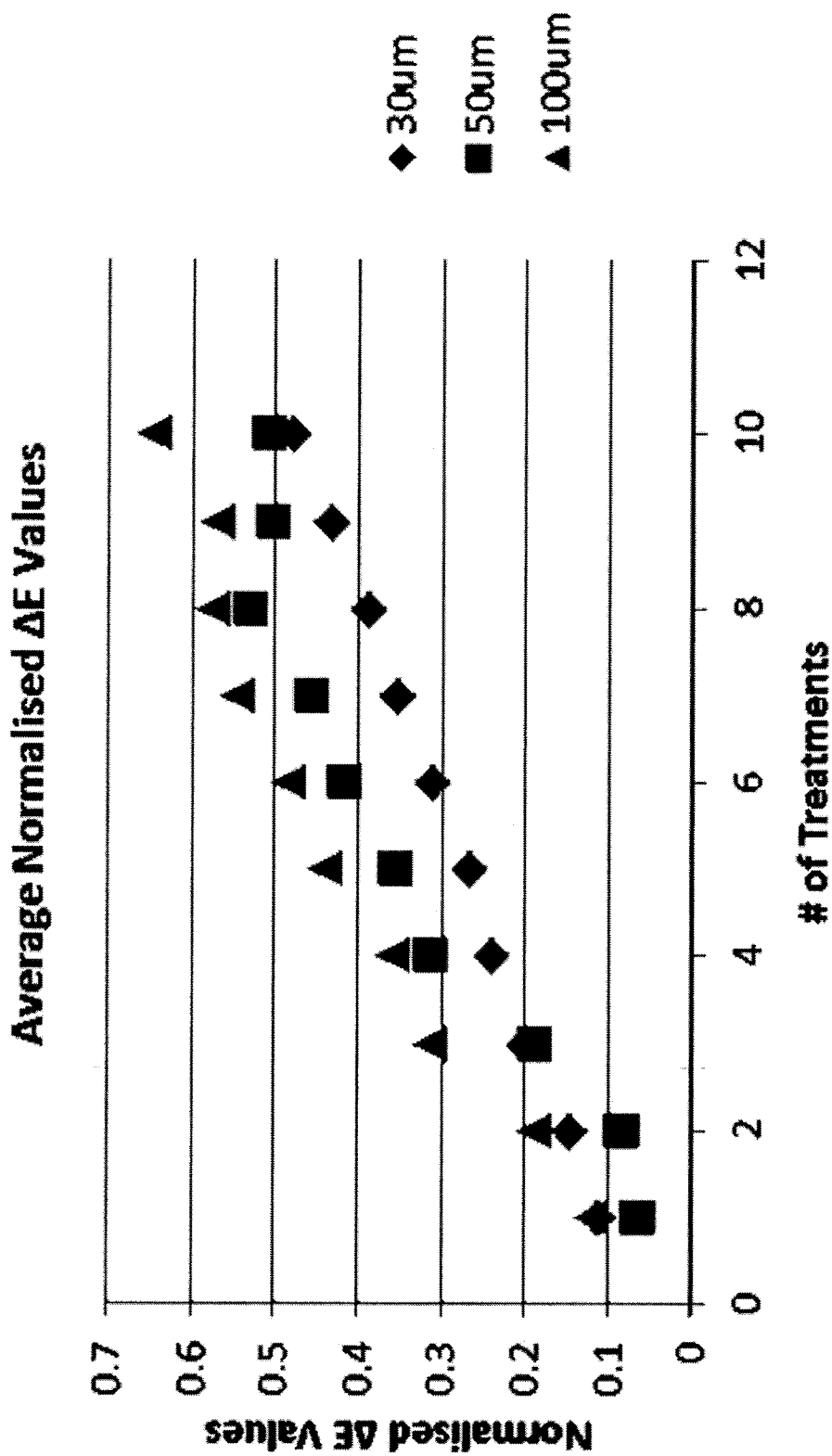
FIG. 16 is a graph illustrating the effect of applied thickness on whitening effect.

An in vitro study was conducted to determine how applied thickness of the first layer whitening varnish impacts whitening effectiveness. The whitening layer composition was that of Sample 8 in Table 4. The barrier layer was formed from Kraton FG1901 in heptane, with 20 µl applied—theoretically 200 µm thickness when spread over tooth surface (in practice this is 100 µm after evaporation loss). Applied first layer thicknesses of 30 µm, 50 µm, and 100 µm were tested over 10 treatments and normalized ΔE values were calculated. The results are presented in FIG. 16. The results indicated that increasing first layer thickness enhances the whitening effect of treatments.

Each of the documents referred to above is incorporated herein by reference.

Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade. It is to be understood that the upper and lower amount, range, and ratio limits set forth herein may be independently combined. Similarly, the ranges and amounts for each element of the invention may be used together with ranges or amounts for any of the other elements. As used herein any member of a genus (or list) may be excluded from the claims.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A method of treating teeth, said method comprising providing an oral care agent to teeth, said method comprising:
   applying a first composition to the teeth to form a first layer on the teeth, the first composition comprising a first polymer matrix, a first solvent, and said oral care agent, wherein the first polymer matrix and the oral care agent are soluble in the first solvent;
   drying or curing the first composition by evaporating the first solvent during or after applying the first composition to the teeth;
   applying a second composition over the first layer to form the second layer on the first layer after drying or curing the applied first composition, the second composition configured to be spaced from a surface of the teeth by the first layer, the second composition comprising a second polymer matrix and a second solvent different from the first solvent, the oral care agent and the first polymer matrix being insoluble in the second solvent and the second polymer matrix being insoluble in the first solvent; and
   drying or curing the second composition by evaporating the second solvent after drying or curing the first composition on the teeth;
   wherein the first and second solvents are different insofar as the second solvent does not cause redissolution of the first layer thereby avoiding intermixing of the compositions of the first and second layers when applied to the teeth, and wherein the first polymer matrix comprises a hydrophilic material and the second polymer matrix comprises a hydrophobic material.

* * * * *